United States Patent
Landry et al.

(10) Patent No.: US 9,675,469 B2
(45) Date of Patent: **\*Jun. 13, 2017**

(54) EXPANDABLE INTERBODY FUSION DEVICE

(71) Applicant: SPINE WAVE, INC., Shelton, CT (US)

(72) Inventors: Michael Landry, Austin, TX (US); Steve Wysocki, Stratford, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,007

(22) Filed: Nov. 12, 2015

(65) Prior Publication Data
US 2016/0058570 A1   Mar. 3, 2016

Related U.S. Application Data

(60) Continuation of application No. 14/339,978, filed on Jul. 24, 2014, now Pat. No. 9,192,484, which is a
(Continued)

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/442* (2013.01); *A61F 2/4455* (2013.01);
(Continued)

(58) Field of Classification Search
USPC .......................................... 623/17.11, 17.16
See application file for complete search history.

(56) References Cited

U.S. PATENT DOCUMENTS 3,486,505 A    12/1969   Morrison
4,524,766 A     6/1985   Petersen
(Continued)

FOREIGN PATENT DOCUMENTS

EP    0621020    10/1994
FR    2639823     6/1990
(Continued)

OTHER PUBLICATIONS

Medtronic Sofamor Danek, Verte-Stack PEEK Stackable Corpectomy Device, Surgical Technique (date unknown), 8 pages.
(Continued)

*Primary Examiner* — Jan Christopher Merene
(74) *Attorney, Agent, or Firm* — Hoffmann & Baron, LLP

(57) ABSTRACT

An expandable interbody fusion device includes superior and inferior plates that are configured to receive a sequentially inserted stack of expansion members or wafers. The superior and inferior plates include features that at least initially interlock the two plates until the superior plate is dislodged by pressure from the growing wafer stack. The wafers include features on their top and bottom surfaces that interlock the wafers in multiple degrees of freedom so that the wafer stack is not disrupted when the fusion device is fully expanded. Each wafer also includes features that interlock with the inferior plate until the wafer id dislodged by sequential introduction of another wafer.

11 Claims, 38 Drawing Sheets

Related U.S. Application Data continuation of application No. 14/161,781, filed on Jan. 23, 2014, now Pat. No. 9,095,446, which is a continuation of application No. 13/092,334, filed on Apr. 22, 2011, now Pat. No. 8,641,767, which is a division of application No. 11/211,346, filed on Aug. 25, 2005, now Pat. No. 7,931,688.

(60) Provisional application No. 60/604,422, filed on Aug. 25, 2004.

(51) Int. Cl.
 *A61B 17/02* (2006.01)
 *A61F 2/30* (2006.01)

(52) U.S. Cl.
 CPC ..... *A61F 2/4611* (2013.01); *A61B 2017/0256* (2013.01); *A61F 2/4465* (2013.01); *A61F 2002/3052* (2013.01); *A61F 2002/30383* (2013.01); *A61F 2002/30476* (2013.01); *A61F 2002/30492* (2013.01); *A61F 2002/30556* (2013.01); *A61F 2002/30599* (2013.01); *A61F 2002/30601* (2013.01); *A61F 2002/30904* (2013.01); *A61F 2220/0025* (2013.01); *A61F 2250/0009* (2013.01); *A61F 2250/0063* (2013.01)

(56) References Cited

U.S. PATENT DOCUMENTS

| | | | |
|---|---|---|---|
| 4,683,476 A | 7/1987 | Ferrari et al. | |
| 4,736,738 A | 4/1988 | Lipovsek et al. | |
| 4,755,797 A | 7/1988 | Kanaya | |
| 4,863,476 A | 9/1989 | Shepperd | |
| 4,888,024 A | 12/1989 | Powlan | |
| 5,059,193 A | 10/1991 | Kuslich | |
| 5,192,326 A | 3/1993 | Bao et al. | |
| 5,192,327 A | 3/1993 | Brantigan | |
| 5,197,971 A | 3/1993 | Bonutti | |
| 5,298,254 A | 3/1994 | Prewett et al. | |
| 5,431,658 A | 7/1995 | Moskovich | |
| 5,439,684 A | 8/1995 | Prewett et al. | |
| 5,505,732 A | 4/1996 | Michelson | |
| 5,514,180 A | 5/1996 | Heggeness et al. | |
| 5,522,899 A | 6/1996 | Michelson | |
| 5,554,191 A | 9/1996 | Lahille et al. | |
| 5,571,109 A | 11/1996 | Bertagnoli | |
| 5,591,235 A | 1/1997 | Kuslich | |
| 5,620,458 A | 4/1997 | Green et al. | |
| 5,645,599 A | 7/1997 | Samani | |
| 5,653,763 A | 8/1997 | Errico et al. | |
| 5,658,335 A | 8/1997 | Allen | |
| 5,702,454 A | 12/1997 | Baumgartner | |
| 5,755,797 A | 5/1998 | Baumgartner | |
| 5,756,127 A | 5/1998 | Grisoni et al. | |
| 5,836,948 A | 11/1998 | Zucherman et al. | |
| 5,860,977 A | 1/1999 | Zucherman et al. | |
| 5,865,848 A * | 2/1999 | Baker .................. A61F 2/4455 606/247 |
| 5,891,147 A | 4/1999 | Moskovitz et al. | |
| 5,904,719 A | 5/1999 | Errico et al. | |
| 5,951,553 A | 9/1999 | Betz et al. | |
| 5,980,522 A | 11/1999 | Koros et al. | |
| 6,033,411 A | 3/2000 | Preissman | |
| 6,045,579 A | 4/2000 | Hochshuler et al. | |
| 6,066,154 A | 5/2000 | Reiley et al. | |
| 6,074,390 A | 6/2000 | Zucherman et al. | |
| 6,102,950 A | 8/2000 | Vaccaro | |
| 6,110,179 A | 8/2000 | Flivik et al. | |
| 6,110,210 A | 8/2000 | Norton et al. | |
| 6,159,211 A | 12/2000 | Boriani et al. | |
| 6,159,244 A | 12/2000 | Suddaby et al. | |
| 6,176,882 B1 | 1/2001 | Biedermann et al. | |
| 6,190,414 B1 | 2/2001 | Young et al. | |
| 6,193,757 B1 | 2/2001 | Foley et al. | |
| 6,200,347 B1 | 3/2001 | Anderson et al. | |
| 6,241,771 B1 | 6/2001 | Gresser et al. | |
| 6,273,916 B1 | 8/2001 | Murphy | |
| 6,279,916 B1 | 8/2001 | Stecher | |
| 6,287,308 B1 | 9/2001 | Betz et al. | |
| 6,287,309 B1 | 9/2001 | Baccelli et al. | |
| 6,387,130 B1 | 5/2002 | Stone et al. | |
| 6,395,034 B1 | 5/2002 | Suddaby | |
| 6,402,750 B1 | 6/2002 | Atkinson et al. | |
| 6,419,705 B1 | 7/2002 | Erickson | |
| 6,432,107 B1 | 8/2002 | Ferree | |
| 6,436,142 B1 | 8/2002 | Paes et al. | |
| 6,447,544 B1 | 9/2002 | Michelson | |
| 6,478,800 B1 | 11/2002 | Fraser et al. | |
| 6,488,710 B2 | 12/2002 | Besselink | |
| 6,500,205 B1 | 12/2002 | Michelson | |
| 6,562,074 B2 | 5/2003 | Gerbec et al. | |
| 6,572,653 B1 | 6/2003 | Simonson | |
| 6,595,998 B2 | 7/2003 | Johnson et al. | |
| 6,620,196 B1 | 9/2003 | Trieu | |
| 6,648,917 B2 | 11/2003 | Gerbec et al. | |
| 6,656,178 B1 | 12/2003 | Veldhuizen et al. | |
| 6,726,691 B2 | 4/2004 | Osorio et al. | |
| 6,740,093 B2 | 5/2004 | Hochschuler et al. | |
| 6,837,904 B2 | 1/2005 | Ralph et al. | |
| 6,852,095 B1 | 2/2005 | Ray | |
| 6,852,126 B2 | 2/2005 | Ahlgren | |
| 6,852,129 B2 | 2/2005 | Gerbec et al. | |
| 6,863,673 B2 | 3/2005 | Gerbec et al. | |
| 6,997,929 B2 | 2/2006 | Manzi et al. | |
| 7,118,580 B1 | 10/2006 | Beyersdorff et al. | |
| 7,153,325 B2 | 12/2006 | Kim et al. | |
| 7,311,713 B2 | 12/2007 | Johnson et al. | |
| 7,682,397 B2 | 3/2010 | Berry et al. | |
| 7,771,473 B2 | 8/2010 | Thramann | |
| 7,780,707 B2 | 8/2010 | Johnson et al. | |
| 8,715,351 B1 | 5/2014 | Pinto | |
| 8,900,312 B2 | 12/2014 | McLean et al. | |
| 2002/0026195 A1 | 2/2002 | Layne et al. | |
| 2002/0107574 A1 | 8/2002 | Boehm, Jr. et al. | |
| 2002/0128716 A1 | 9/2002 | Cohen et al. | |
| 2002/0147497 A1 | 10/2002 | Belef et al. | |
| 2002/0177897 A1 | 11/2002 | Michelson | |
| 2002/0183761 A1 | 12/2002 | Johnson et al. | |
| 2003/0065396 A1* | 4/2003 | Michelson .......... A61F 2/30744 623/17.15 |
| 2003/0130739 A1 | 7/2003 | Gerbec et al. | |
| 2003/0171812 A1 | 9/2003 | Grunberg et al. | |
| 2004/0019354 A1 | 1/2004 | Johnson et al. | |
| 2004/0064144 A1 | 4/2004 | Johnson et al. | |
| 2004/0087947 A1 | 5/2004 | Lim et al. | |
| 2004/0153065 A1 | 8/2004 | Lim | |
| 2004/0220580 A1 | 11/2004 | Johnson et al. | |
| 2005/0027364 A1 | 2/2005 | Kim et al. | |
| 2005/0038512 A1* | 2/2005 | Michelson .......... A61F 2/30744 623/17.11 |
| 2005/0060034 A1 | 3/2005 | Berry et al. | |
| 2005/0107878 A1 | 5/2005 | Conchy | |
| 2005/0125062 A1 | 6/2005 | Biedermann et al. | |
| 2005/0149194 A1 | 7/2005 | Ahlgren | |
| 2005/0228500 A1 | 10/2005 | Kim et al. | |
| 2006/0122701 A1* | 6/2006 | Kiester .................. A61F 2/447 623/17.11 |
| 2006/0129244 A1 | 6/2006 | Ensign | |
| 2008/0300598 A1 | 12/2008 | Barreiro et al. | |
| 2010/0179656 A1 | 7/2010 | Theofilos | |

FOREIGN PATENT DOCUMENTS

| | | |
|---|---|---|
| FR | 2719763 | 11/1995 |
| WO | 9902214 | 1/1999 |

OTHER PUBLICATIONS

Signus Medical, Tetris, Sep. 2003, 1 page.

(56) References Cited

OTHER PUBLICATIONS

Blackstone Medical, Inc. Construx Peek VBR System, 2005, 1 page.
Globus Medical, Sustain R Small (date unknown), 6 pages.
Braddley, S. and Cullen, J.C., "The Use of Methylmethacrylate in the Treatment of Giant Tumors of the Proximal Tibia", Aust. N.Z. J. Surg. vol. 49, No. 1, Feb. 1979, 3 pages.
Campanacci, M., Gui, Rainer, L. and Savini, R., "The Treatment of Tibial Plateau Fractures", Chi. Org. Mov. 72(3), Dec. 1975 (Italian text) (pp. 234-256) English translation.
Kyphon Surgical Technique Manual, 1999, pp. 5, 6, 9, 16-19.
Kyphon Vertebral Treatment Notebook, date unknown, 9 pages.
Kyphon web page, www.kyphon.com, Mar. 13, 2001, 1 page.
AOM Techniques Manual, date unknown, 11 pages.
http://www.thefreedictionary.com/constrict, definition of "constrict", accessed Apr. 16, 2015.
www.thefreedictionary.com/elongate, definition of "elongate", accessed Jul. 9, 2015.

* cited by examiner

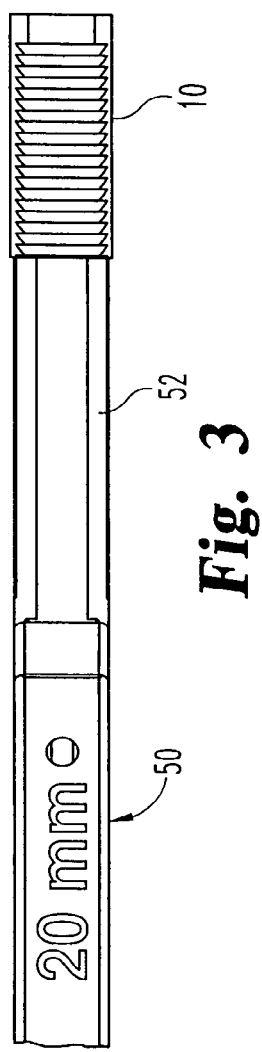
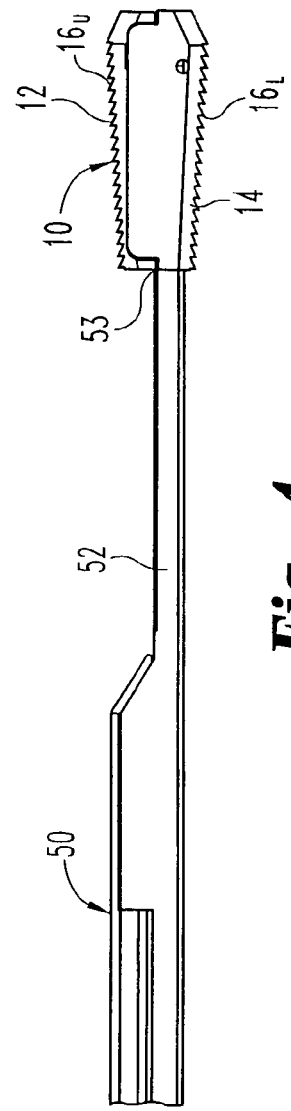
Fig. 3
Fig. 4

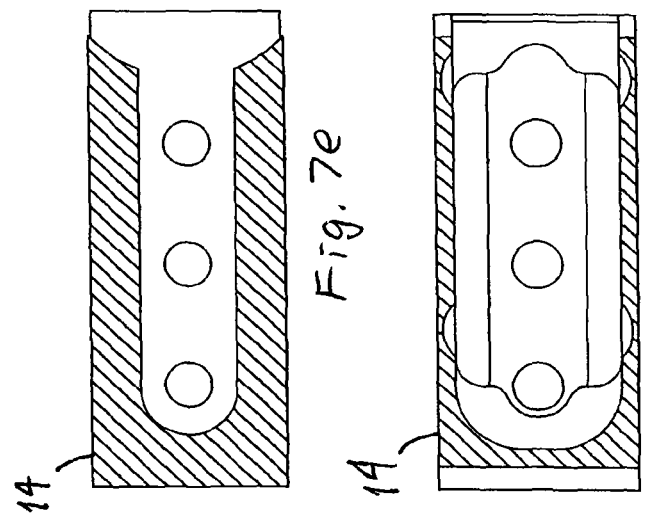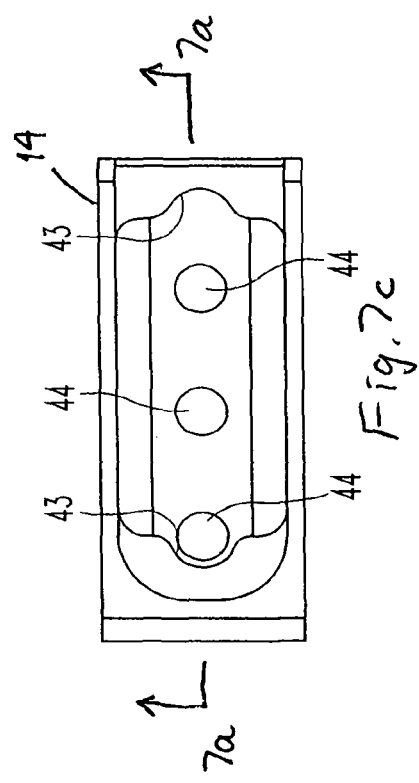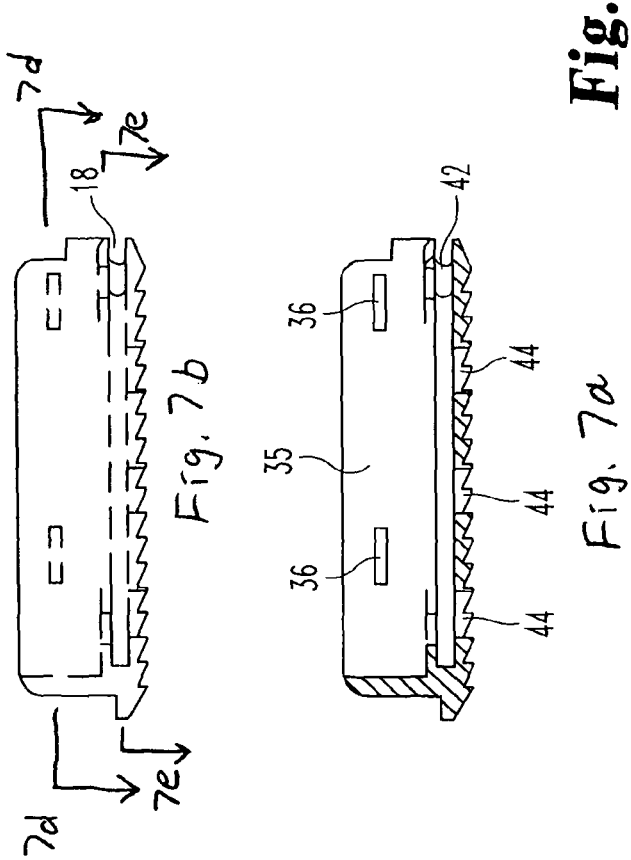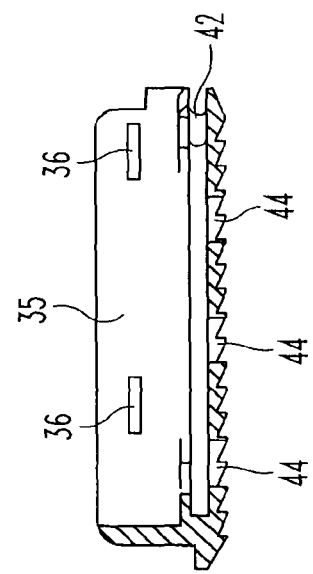
Fig. 7

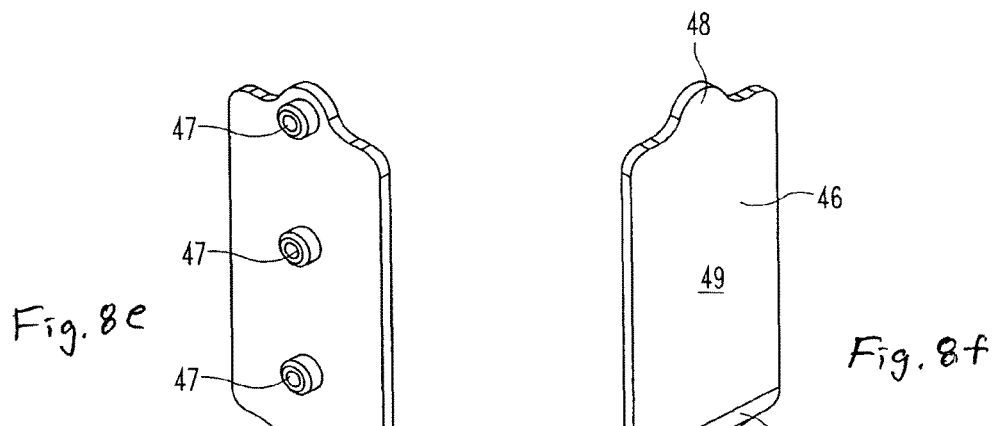
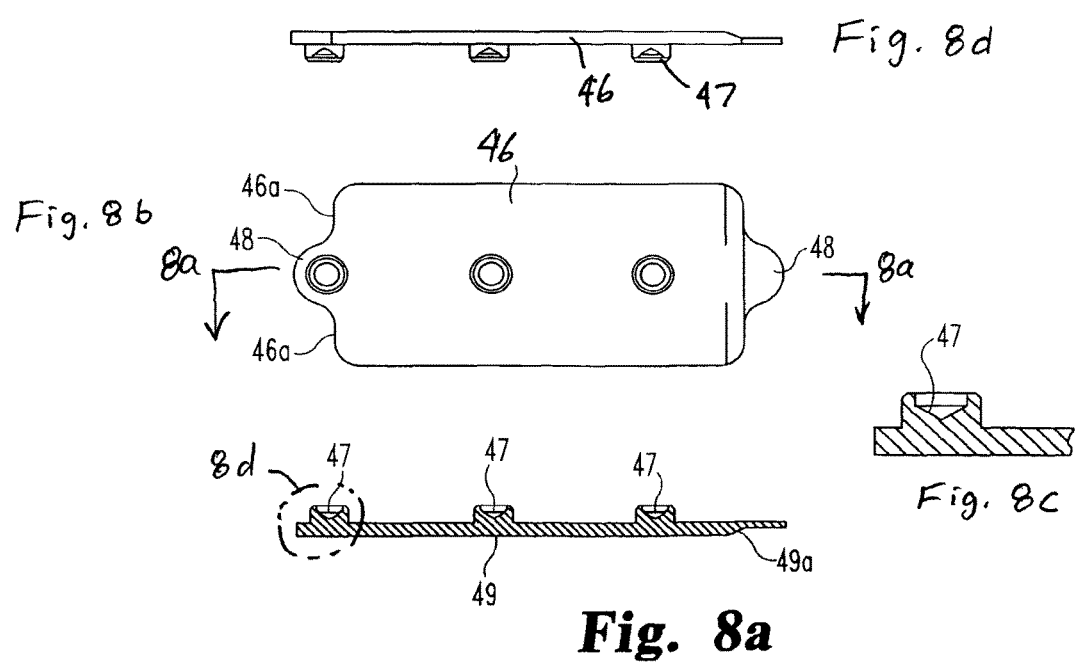

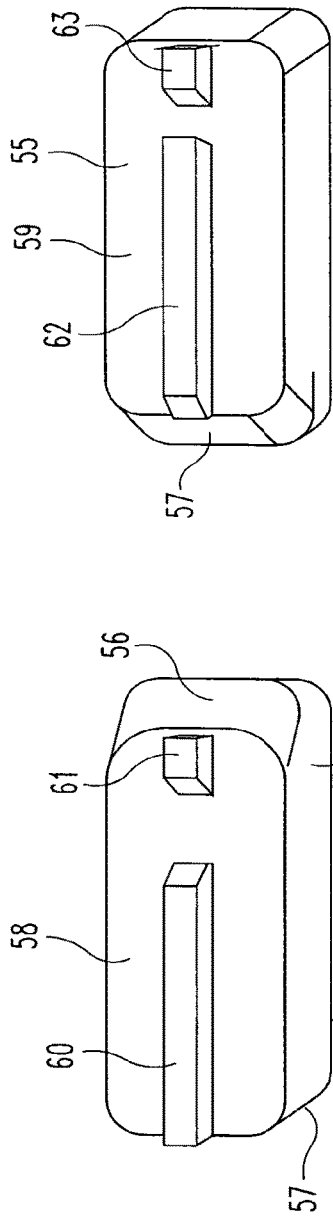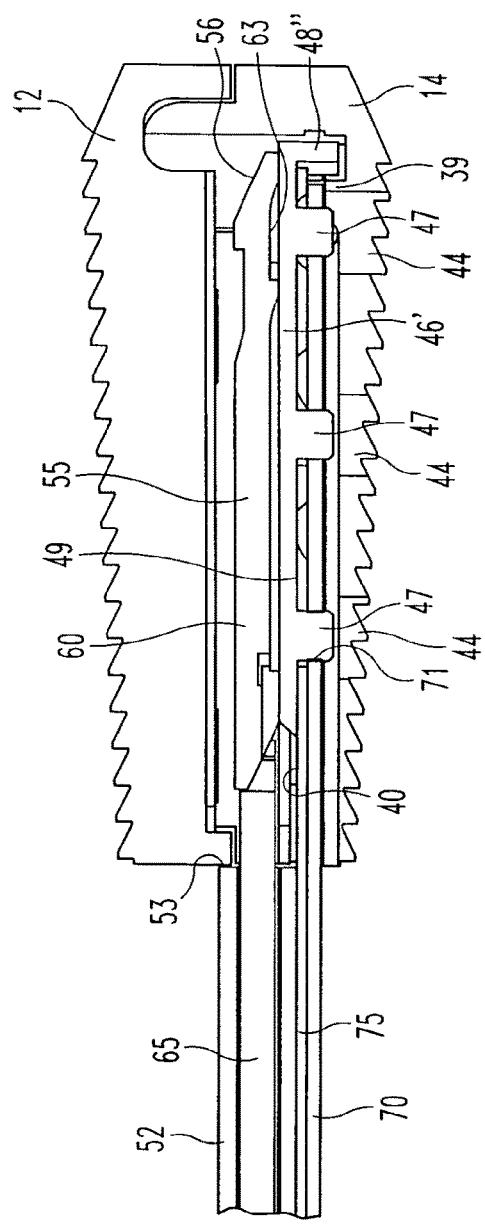

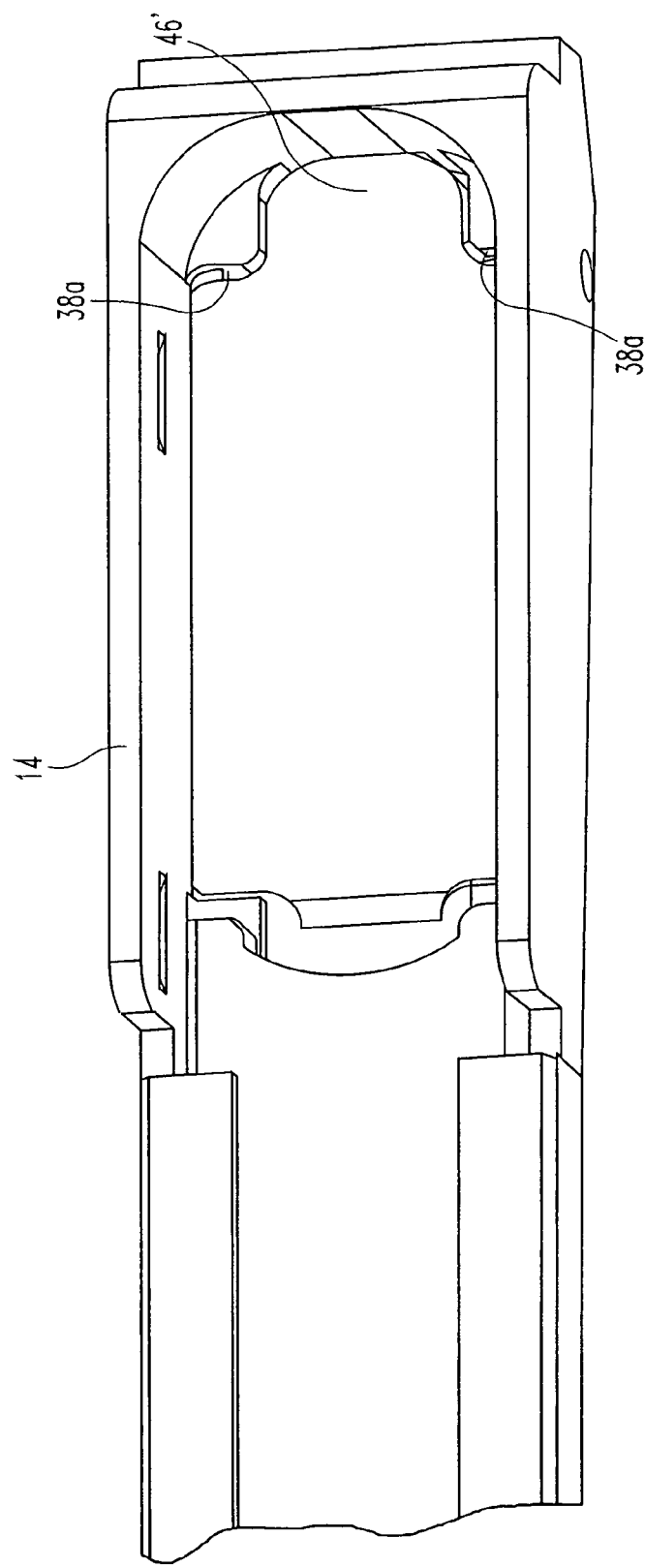

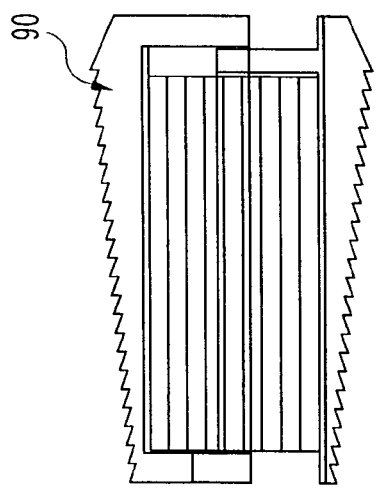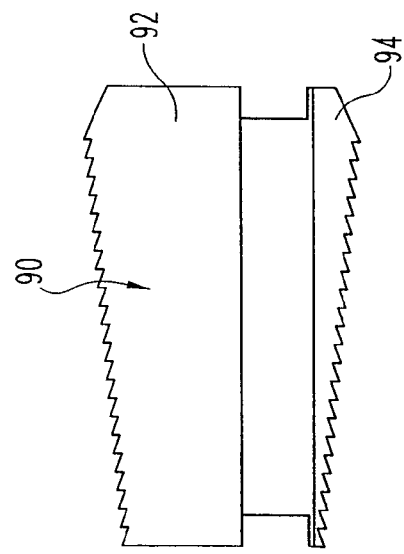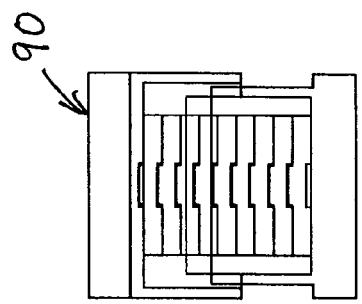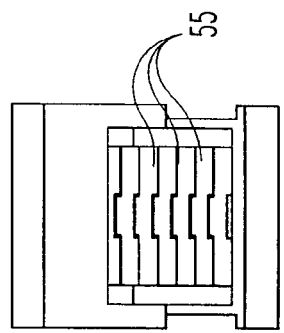
Fig. 22

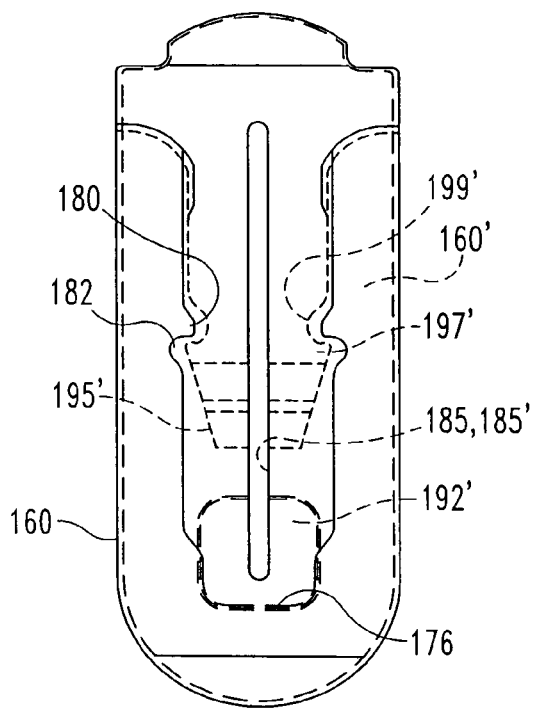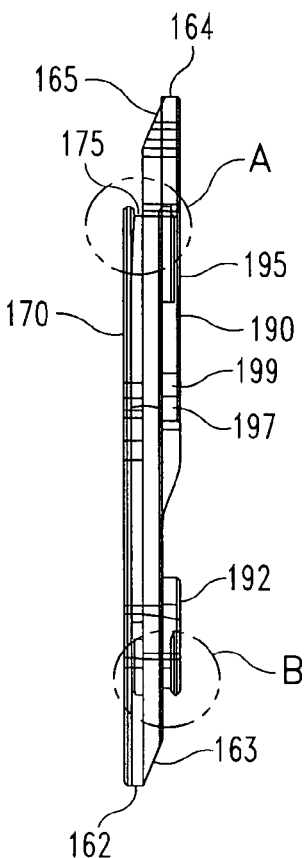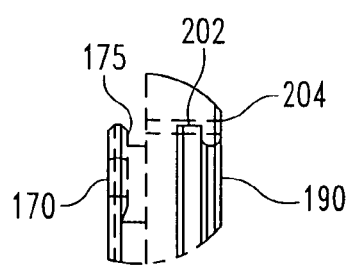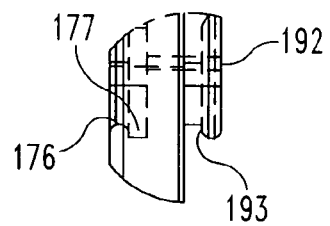
*Fig. 31*  *Fig. 32*  *Fig. 33*  *Fig. 34*

EXPANDABLE INTERBODY FUSION DEVICE

CROSS-REFERENCES TO RELATED APPLICATIONS

This application is a continuation of U.S. patent application Ser. No. 14/339,978, filed on Jul. 24, 2014, now U.S. Pat. No. 9,192,484, which is a continuation of U.S. patent application Ser. No. 14/161,781, filed on Jan. 23, 2014, now U.S. Pat. No. 9,095,446, which is a continuation of U.S. patent application Ser. No. 13/092,334, filed on Apr. 22, 2011, now U.S. Pat. No. 8,641,767, which is a division of U.S. application Ser. No. 11/211,346, filed Aug. 25, 2005, now U.S. Pat. No. 7,931,688, which claims priority to U.S. Provisional Application No. 60/604,422, filed on Aug. 25, 2004, and entitled "Expandable Interbody Fusion Device". The disclosures of these applications are incorporated herein by reference.

BACKGROUND OF THE INVENTION

The present invention relates to devices and methods for distraction and stabilization of tissue surfaces, and most particularly for stabilization of the intervertebral disc space.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intra-discal space, otherwise the space may collapse resulting in damage to the nerves extending along the spinal column.

In order to prevent this disc space collapse, the intra-discal space has been filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique once fusion has occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intra-discal implant that could be used to replace a damaged disc and yet maintain the stability of the disc interspace between the adjacent vertebrae, at least until complete arthrodesis is achieved. These "interbody fusion devices" have taken many forms, but many have had difficulty in achieving fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

The interbody fusion devices (IBFDs) that have overcome these difficulties are typically bulky, at least with respect to the intervertebral space. In particular, these devices have been configured to completely fill the space and to restore the normal spinal anatomy at the instrumented level. One drawback of this approach is that the implant device is not exactly sized to the anatomy of the particular patient, thus typically requiring pre-distraction of opposed vertebrae in order to increase the disc space for device implantation. While a collection of differently sized IBFDs can be provided, it is unwieldy and impractical to provide an IBFD sized for every intervertebral disc space height.

Another drawback of these prior devices is that the surgical insertion site must be at least as big as the IBFD. Minimally invasive and working channel surgical techniques have been recently developed that have significantly reduced the surgical invasion, but even more improvement is needed. The present invention provides an IBFD that achieves all of the benefits of prior IBFD designs, while also addressing the above-noted drawbacks.

SUMMARY OF THE INVENTION

In order to address these drawbacks, the present invention contemplates a device for distracting a body tissue space between opposing tissue surfaces, comprising an upper plate having an outer surface configured to contact one of the opposing surfaces and a lower plate having an outer surface configured to contact the other of the opposing surfaces, the lower plate having opposite side walls configured to removably support the upper plate thereon. The upper and lower plates combine to define a cavity when the upper plate is supported on the lower plate. The lower plate includes a support surface for supporting at least one expansion member, or wafer, within the cavity, and a channel communicating with the cavity that is configured to receive an expansion member conveyed therethrough for placement on the surface of the lower plate.

The upper plate defines an upper surface for contacting an uppermost expansion member within the cavity to displace the upper plate from the lower plate as additional expansion members are conveyed along the channel. In one aspect of the invention, a releasable engagement feature is provided between the upper plate and the lower plate that is configured to hold the upper and lower plates together until the upper plate is displaced by the uppermost expansion member. In one embodiment, the releasable engagement feature includes at least one male element and corresponding mating female element defined between the upper plate and the lower plate. In this embodiment, the male element may be a rib defined on each side wall of the lower plate and the female element may be a corresponding recess.

The upper plate may be provided with a hub sized to fit between the side walls of the lower plate. The recess for the releasable engagement feature then includes at least one groove defined on opposite sides of the hub that is configured for releasable engagement with a rib on a corresponding side wall of the lower plate. In one specific embodiment, the recess includes at least two grooves offset from each other on opposite sides of the hub, each of the grooves configured for releasable engagement with the rib on a corresponding side wall of the lower plate.

In another aspect of the invention, an expansion member is provided for use with the expandable device that comprises a wafer sized to be conveyed through the channel and to be supported on the support surface of the lower plate. The wafer has opposite side walls configured to form part of a releasable engagement feature between the wafer and the lower plate. In certain embodiments, the wafer has opposite side walls, each defining a mating recess configured for releasable engagement with the rib defined on each side wall of the lower plate.

In yet another feature of the invention, an expansion member for sequential insertion into a space between opposing tissue surfaces to be distracted is provided that comprises an elongated body having an upper surface and an opposite lower surface, and an insertion end and an opposite trailing end. A female feature is defined on one of the upper and lower surface, the female feature having an opening at the trailing end, while a male feature is defined on the other of the upper and lower surface that is configured for insertion through the opening. In accordance with this embodiment, resilient interlocking features are defined between the female and male features for resiliently interlocking adjacent elongated bodies when the male feature of one body is inserted into the female feature through the opening.

The female feature may be an elongated recess, while the male feature may constitute an elongated boss configured to be received within the recess. The resilient interlocking features include at least one latch element and indentation adjacent the latch element defined at opposite sides of the recess, and at least one corresponding mating indentation and mating latch element adjacent the mating indentation defined at opposite sides of the boss. This mating indentation and mating latch combination is arranged so that the latch element is received in the mating indentation and the mating latch element is received in the indentation when the elongated boss is received in the elongated recess.

In one particular embodiment, the resilient interlocking features includes three of the latch elements and indentations spaced along the length of the elongated recess, and three of the corresponding mating indentations and mating latch elements comparably spaced along the length of the boss. The latch elements on the opposite sides of the elongated recess define a width therebetween, with the width decreasing between successive ones of the latch elements. Similarly, the mating latch elements on the opposite sides of the elongated boss define a width therebetween, with that width decreasing between successive ones of the mating latch elements.

In certain embodiments, the resilient interlocking features of the wafer body include a slot defined through the wafer extending along at least a portion of the length of the elongated boss. The slot is situated between the mating indentation and the mating latch element on the opposite sides of the boss so that wafer may contract slightly as the interlocking feature of one surface is pushed into engagement with the interlocking feature of the opposite surface on an adjacent wafer as the wafers are sequentially inserted into the tissue space.

The resilient interlocking features lock sequential wafers against relative movement along the length of the wafers. In another aspect, features are provided that also lock sequential wafers against relative movement perpendicular to their length. Thus, in one embodiment, the female feature is an elongated recess including the opening at one end and an end wall at end opposite the opening, the end wall defining a recess undercut. The male feature in this embodiment is an elongated boss configured to be received within the recess and having a leading boss defining a boss undercut arranged to interlock with the recess undercut when the boss is within the recess. The elongated recess may also define recess side undercuts in opposite sides of the recess adjacent the opening, and the elongated boss may define boss side undercuts at opposite sides of the boss and arranged to interlock with the recess side undercuts when the boss is within the recess.

In still another embodiment of the invention, an expansion member for sequential insertion into a space between opposing tissue surfaces to be distracted comprises an elongated body having an upper surface and an opposite lower surface, and an insertion end and an opposite trailing end. A female feature is defined on one of the upper and lower surface, the female feature having an opening at the trailing end, while a male feature is defined on the other of the upper and lower surface and configured for insertion through the opening. In this embodiment, a locking feature is defined between the female and male features for locking adjacent elongated bodies against relative movement along the length of the bodies when the male feature of one body is inserted into the female feature through the opening. The locking feature preferably includes resiliently deformable elements defined on the female and male features. The embodiment may also include an interlocking feature defined between the female and male features for interlocking adjacent elongated bodies against relative movement perpendicular to the length of the bodies when the male feature of one body is inserted into the female feature through the opening.

An expansion member for sequential insertion into a space between opposing tissue surfaces to be distracted in another aspect of the invention comprises an elongated body having an upper surface, an opposite lower surface, an insertion end and an opposite trailing end, wherein the body includes a leading boss projecting above the upper surface adjacent the insertion end and a recess defined in the lower surface beneath the boss, the leading boss defining a rear undercut opposite the insertion end. The body further defines a slot therethrough terminating at one end beneath the rear undercut and including at its opposite end a flexible arm extending into the slot toward the boss and having an end positioned beneath the undercut. With this embodiment, when two of the expansion members are coupled, the boss of a lowermost expansion member fits within the recess of the uppermost expansion member, and the flexible arm of the uppermost expansion member is trapped between the undercut of the boss of the uppermost member and the boss of the lowermost expansion member.

In a further embodiment, an expandable interbody fusion device for implantation into the intradiscal space between the opposing vertebral bodies in a spine comprises an upper plate having an outer surface configured to contact an upper vertebral body and a lower plate having an outer surface configured to contact a lower vertebral body, a support surface and an opening communicating with the support surface. The upper plate and the lower plate are configured to be releasably engaged and define a cavity between the upper plate and the support surface of the lower plate. The fusion device further comprises at least two expansion members sized to be sequentially received through the opening onto the support surface, one expansion member beneath an immediately prior expansion member to raise the immediately prior expansion member. In one feature of this embodiment, a releasable engagement is defined between the lower plate and each of the expansion members. This releasable engagement is operable to engage the immediately prior expansion member raised by the one expansion member.

It is one object of the invention to provide an improved expandable device that may be used to distract the space between two body tissue surfaces. A further object resides in aspects of the expandable device that allow for control expansion of the device, especially by sequential insertion of interlocking expansion members or wafers.

A further object of the invention is to provide expansion members that interlock in multiple degrees of freedom. One benefit of this feature is that the wafers become interlocked upon sequential insertion, and do not become dislodged or disassociated with each other during expansion of the expandable device or after the device is complete in situ. Other objects and benefits of the invention will become apparent upon consideration of the following written description taken together with the accompanying figures.

DESCRIPTION OF THE FIGURES

FIG. 3 is a top view of the IBFD of FIGS. 1-2 mounted on an insertion apparatus in accordance with one aspect of the invention.

FIG. 4 is a side view of the IBFD and insertion apparatus shown in FIG. 3.

FIGS. 7a-7e include side, top and cross-sectional views of the inferior endplate portion of the IBFD shown in FIGS. 6a-6e.

FIGS. 11a, b are top perspective and bottom views of a wafer for introduction into the IBFD of FIGS. 1-2 using the insertion apparatus as shown in FIGS. 3-4 and 9.

FIG. 12 is a side cut-away view of the structure shown in FIG. 9.

FIGS. 16b-d are top, top perspective and top perspective cut-away views of components of the insertion apparatus engaged with the inferior endplate portion and including the track connector of FIG. 8b prior to wafer insertion.

FIGS. 22a-d include side and end views of the IBFD shown in FIGS. 21a-21b.

FIG. 31 is a bottom elevational view of the interlocking wafer shown in FIGS. 28-30 with a second wafer engaged thereto, as depicted in phantom liens.

FIG. 32 is a side elevational view of the interlocking wafer shown in FIGS. 28-30.

FIG. 33 is an enlarged partial side view of the region A of the wafer shown in FIG. 32.

FIG. 34 is an enlarged partial side view of the region B of the wafer shown in FIG. 32.

DESCRIPTION OF THE PREFERRED EMBODIMENTS

Figure 1:
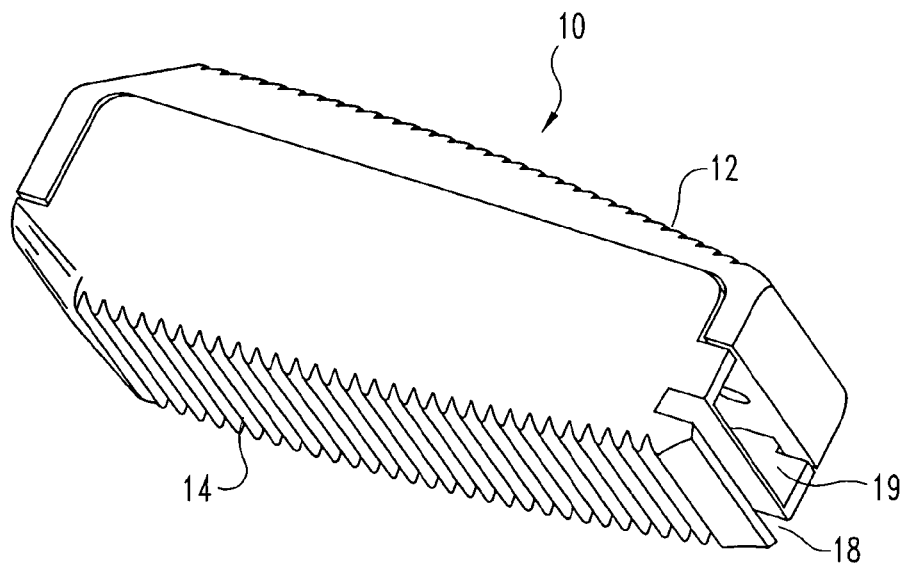
FIG. 1 is a bottom perspective view of an interbody fusion device (IBFD) according to one embodiment of the invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
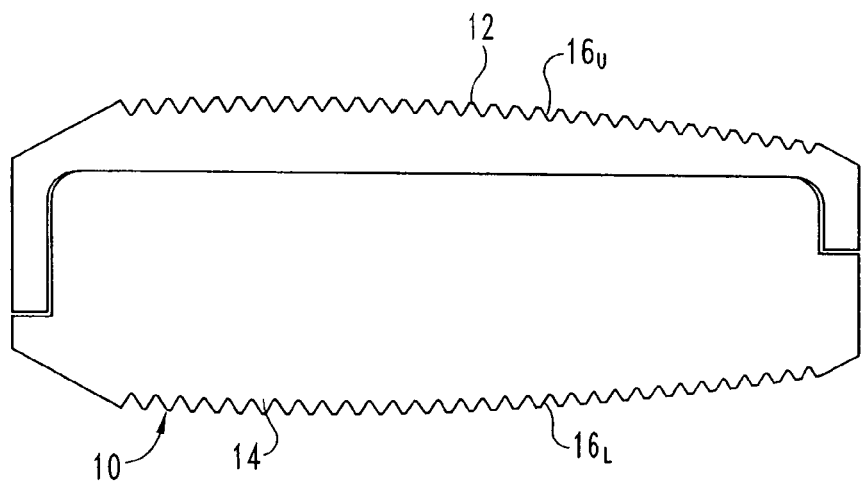
FIG. 2 is a side view of the IBFD shown in FIG. 1.
Figure 5F:
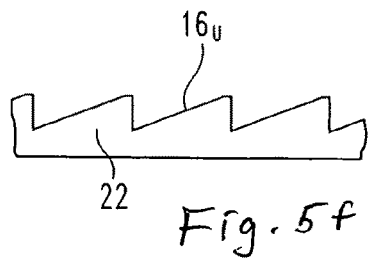
FIGS. 5a-5f include perspective, side, end, top and bottom views of a superior endplate portion of the IBFD shown in FIGS. 1-2, and including a cross-sectional and enlarged view of portions thereof.
Figure 5D:
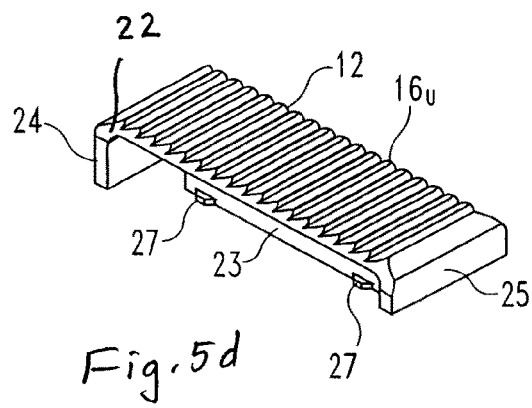
Figure 5E:
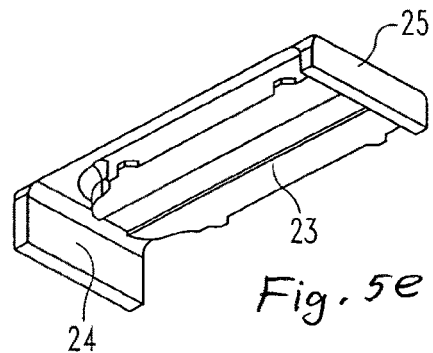
Figure 5C:
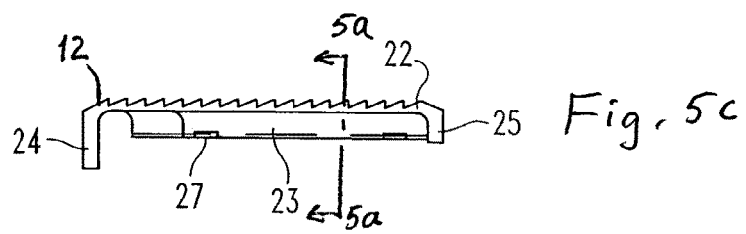
Figure 5B:
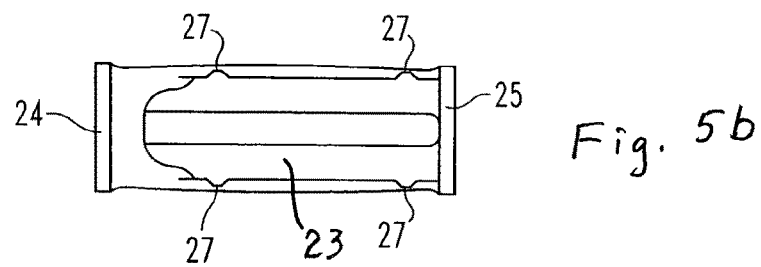
Figure 5A:
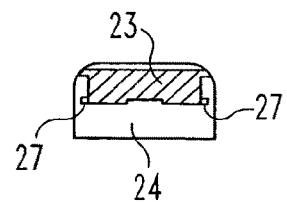
Figure 6D:
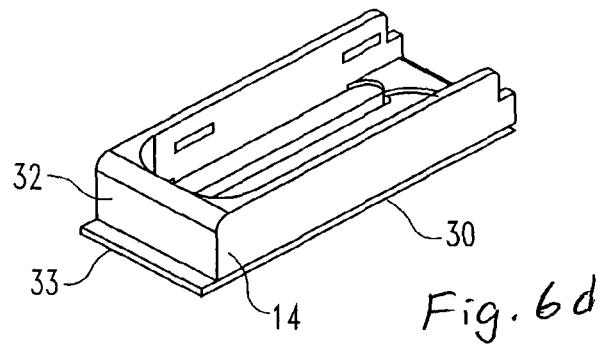
FIGS. 6a-6e include perspective, side, end, top and bottom views of an inferior endplate portion of the IBFD shown in FIGS. 1-2, including an enlarged view of a portion thereof.
Figure 6C:
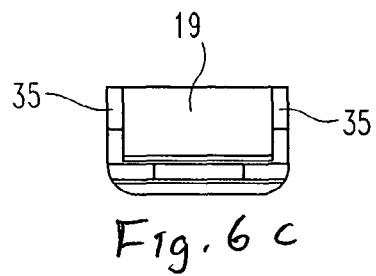
Figure 6E:
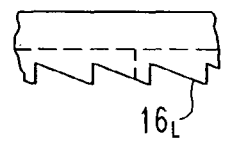
Figure 6B:
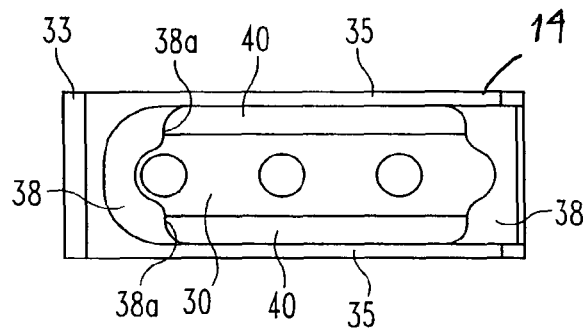
Figure 6A:
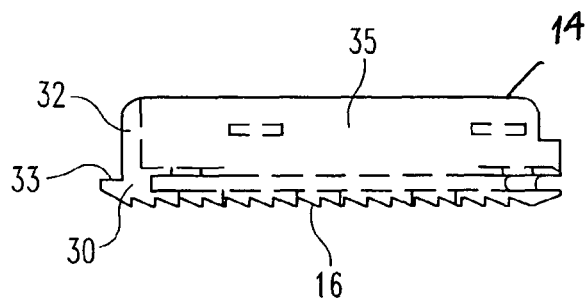

In accordance with one embodiment of the invention, an expandable distraction device in the form of an interbody fusion device (IBFD) 10 includes a superior endplate 12 and an inferior endplate 14 that define a wafer cavity 19, as shown in FIGS. 1-2. The superior and inferior surfaces of the endplates define engagement ribs $16_U$ and $16_L$ that are configured to engage or grip the vertebral endplates of opposed vertebrae in a spine. Preferably, the ribs $16_U$ and $16_L$ are configured to prevent expulsion of the IBFD under normal spinal loads. For instance, the ribs may have a saw tooth shape that is inclined toward the opening through which the IBFD is inserted into the interbody space. Angling the ribs toward the opening also angles them away from the direction of insertion so that the IBFD can be easily inserted into a collapsed space.

The IBFD 10 also defines an inserter cavity 18 that engages a portion of an inserter apparatus 50, as shown in FIGS. 3-4. The inserter apparatus 50 defines a wafer track 52 along which a plurality of wafers, or expansion members, are conveyed to fill the wafer cavity 19.

In accordance with one aspect of the invention, the IBFD 10 has a height across the superior and inferior endplates 12, 14 that is less than the normal anatomic height of a typical intervertebral disc space. The invention contemplates that a series of expansion members, such as wafers, are introduced into the wafer cavity 19 to at least fill all or part of the cavity, and to distract the opposing vertebrae by separating the superior and inferior endplates. Insertion of the wafers separates the endplates to expand the height of the IBFD within the intervertebral or interbody space and to ultimately restore the normal anatomic height of the instrumented disc space.

Details of the superior and inferior endplates can be seen in FIGS. 5-7. Referring to FIGS. 5a-5f, and in particular to FIG. 5d, the superior endplate 12 includes an upper wall 22 on which the engagement ribs $16_U$ are defined. The interior face of the upper wall is thickened in a reinforcement region 23. This region helps maintain the integrity of the superior endplate 12 and provides a strong surface against which a lifting force can be applied by successive insertion of the wafer. Region 23 is also configured to contain and to cooperate with the wafers, as described below, to provide lateral and torsional stability to the wafer stack.

Figure 9:
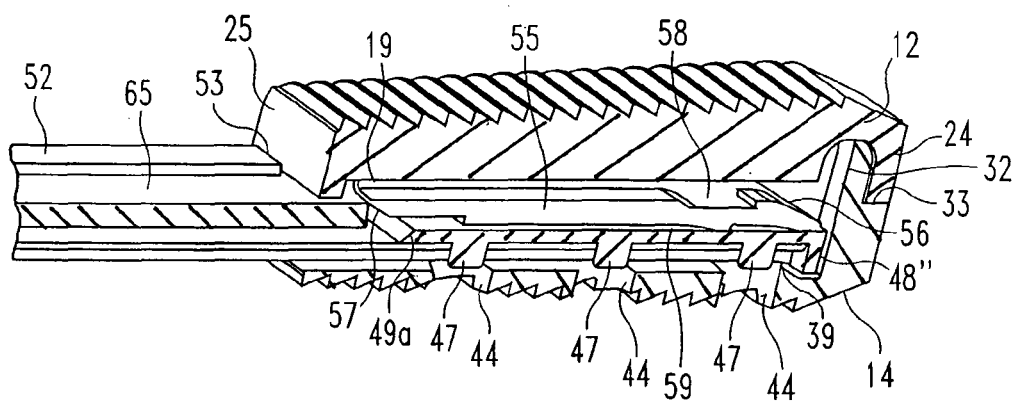
FIG. 9 is a side perspective partial cut-away view of the IBFD and insertion apparatus shown in FIGS. 3-4 with the track connector shown in FIG. 8b in accordance with one embodiment of the invention.

The upper wall terminates in an anatomically anterior end wall 24 and an anatomically posterior end wall 25 that integrate with the inferior endplate 14 as described below. In addition, the reinforcement region 23 defines outwardly and laterally projecting ribs 27 that engage cooperating notches 36 defined in the interior of the inferior endplate 14. Details of the inferior endplate are shown in FIGS. 6-7. The endplate 14 includes a bottom wall 30 on which the engagement ribs $16_L$ are defined. The bottom wall 30 terminates in an end wall 32 and a ledge 33. As shown in FIGS. 2 and 9, the anterior end wall 24 of the superior endplate 12 overlaps the end wall 32 and end ledge 33 when the endplates are initially assembled. The two end walls 24 and 30 overlap over the majority of the height of the end wall 32 so that as the superior and inferior endplates are pushed apart the two endplates remain in contact and continue to define the wafer cavity 19, providing stability to the IBFD as it expands.

The inferior endplate 14 also defines side walls 35 that define the wafer cavity and ultimately help retain the wafers within the cavity as they are sequentially inserted. The inner face of the side walls defines notches 36 that are aligned for engagement by the ribs 27 in the superior endplate 12. Thus, when the IBFD is initially assembled prior to insertion into the interbody space, the ribs and notches 27, 36 hold the two endplates together. The interface between the ribs and notches is adequate to hold the IBFD together as it is inserted into the space, but is sufficiently weak to be dislodged under pressure from the inserted wafers.

The interior of the inferior endplate 14 includes opposite surfaces 38 that structurally reinforce the IBFD under large compressive loads. Slightly offset from the walls 38 are support rails 40 (FIG. 6b) that support the track connector 46 shown in FIGS. 8a-8f. The top surface 49 of the track connector 46 is configured to be superior to surface 38 such that any compressive load from the wafer stack is transmitted through the bottom surface of the track connector to the support rails 40. The end walls 38 of the endplate 14 also form end notches 43 (FIG. 7c) that are complementary to the end edges of the track connector 46 in one embodiment of the invention. The end walls 38 and rails 40 of the endplate 14 define a connector channel 42, as shown in FIG. 7a, which is configured to receive the distal end of the wafer track of inserter apparatus 50, as described below.

The superior and inferior endplates 12, 14 may be formed of a biocompatible material with sufficient strength to support the adjacent vertebrae without fatigue and fracture. Preferably, the two endplates are molded from a biocompatible polymeric material, such as, for example, PEEK or a biocompatible composite material, such as, for example carbon-fiber-reinforced PEEK. The material may also be selected to permit tissue ingrowth to integrate with the vertebral endplates. The endplates can further be formed from a moldable or formable biologic material, such as bone.

In accordance with one aspect of this invention, the IBFD 10 is configured to be introduced into the interbody space by an introducer or inserter apparatus 50. The inserter can be constructed and operated like the insertion apparatus disclosed in U.S. Pat. No. 6,595,998, entitled "Tissue Distraction Device", which issued on Jul. 22, 2003, to the assignee of the present invention. The disclosure of this patent, and particularly its discussion of the wafer inserter, is incorporated herein by reference. Alternatively, the inserter can be constructed and operated like the insertion apparatus disclosed in co-pending application Ser. No. 10/813,819, entitled "Tissue Distraction Device", filed on May 31, 2004, and assigned to the assignee of the present invention. The disclosure of this co-pending application is incorporated herein by reference.

For purposes of illustration, certain details of the inserter 50 will be explained herein. As shown in FIG. 3, the apparatus includes a wafer track 52 along which wafers are conveyed to fill the wafer cavity 19 within the IBFD and ultimately to expand the height of the IBFD. Once the last wafer has been introduced into the IBFD it is necessary to remove the inserter 50. The preferred embodiment of the invention contemplates a track connector 46 that helps to integrate the wafer track 52 with the interior cavity of the IBFD and to provide a support surface for the wafer stack within the IBFD.

Details of the track connector 46 are shown in FIGS. 8a-8f and FIG. 9. In particular, the connector 46 includes connector posts 47 that project downward with the IBFD, as best seen in FIG. 9. These posts engage corresponding openings 71 in an insertion plate 70 (see FIG. 12) to provide an interface between the inserter apparatus 50 and the IBFD. In one embodiment, the track connector 46 defines interface edges 48 at its opposite ends that are configured to conform to wall 38 in the inferior endplate 14 (see FIG. 6b). The track connector may also include end edges 46a flanking the interface edges that contact wall edges 38a of the endplate 14 to limit the movement of the track connector into the endplate. The track support includes a ramp 49a that helps direct incoming wafers upward from the wafer track 52 to the wafer support surface 49 within the IBFD.

Figure 8:
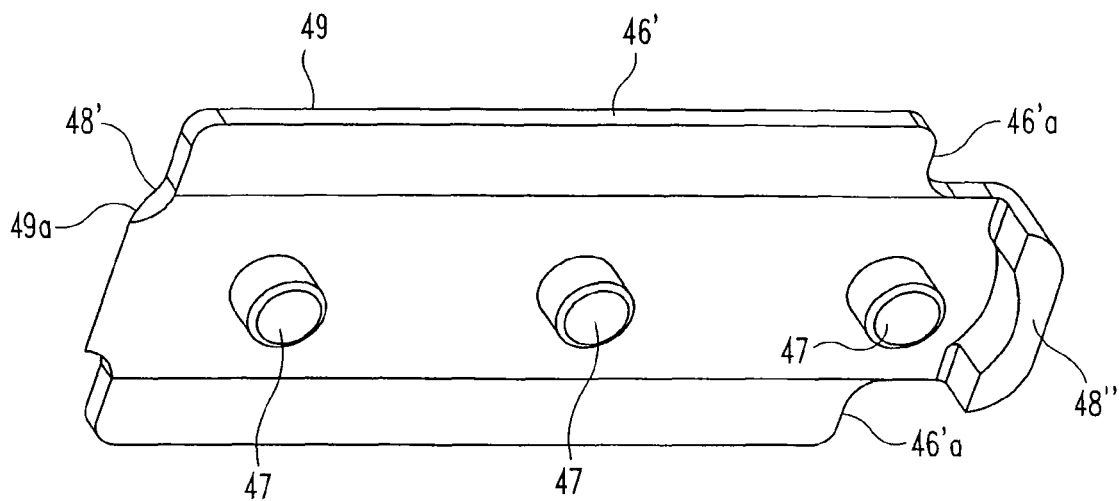
FIGS. 8a-8f include side, top, bottom and perspective views of a track connector used in connection with the insertion apparatus shown in FIGS. 3-4, including cross-sectional views of portions thereof.
FIG. 8g is a bottom perspective view of an alternative embodiment of a track connector used in connection with the insertion apparatus shown in FIGS. 3-4.
Figure 16A:
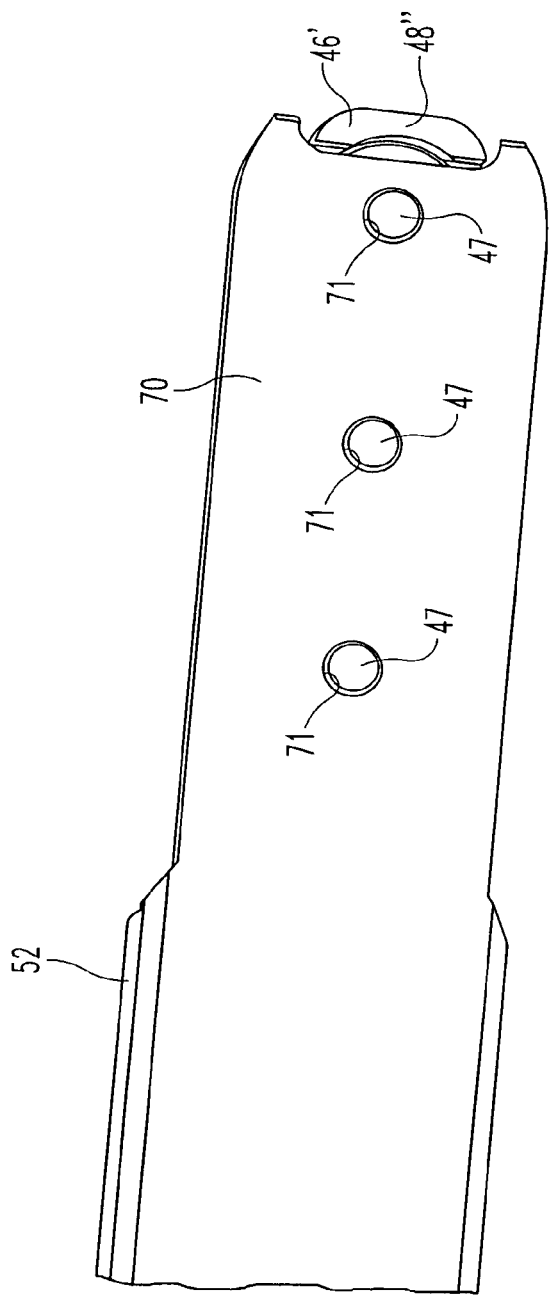
FIG. 16a is a bottom perspective view of the distal end of the wafer track of FIG. 13 with the track connector of FIGS. 8a, 8b mounted thereon.
Figure 16B:
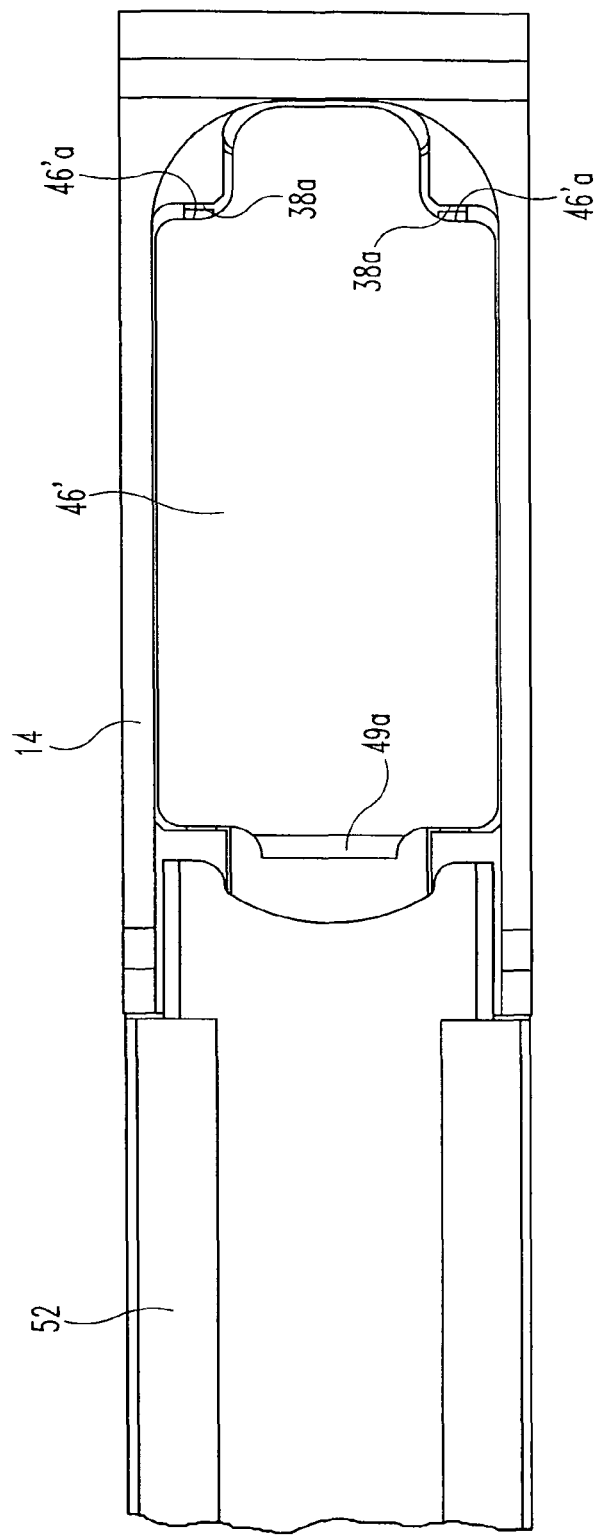

In an alternative embodiment shown in FIG. 8g, a track connector 46' includes a modified proximal end 48' and distal end 48'', but still retains the connector posts 47, wafer support surface 49 and ramp 49a. The modified distal end 48'' catches against a lip 39 formed in the inferior endplate, as shown in FIGS. 9, 12 to prevent removal of the track connector 46' once it is positioned with the assembled IBFD. The distal end of the track connector 46' further defines end edges 46a' that contact the wall edges 38a, as depicted in FIG. 16b, in the same manner as the end edges 46a described above.

Figure 10:
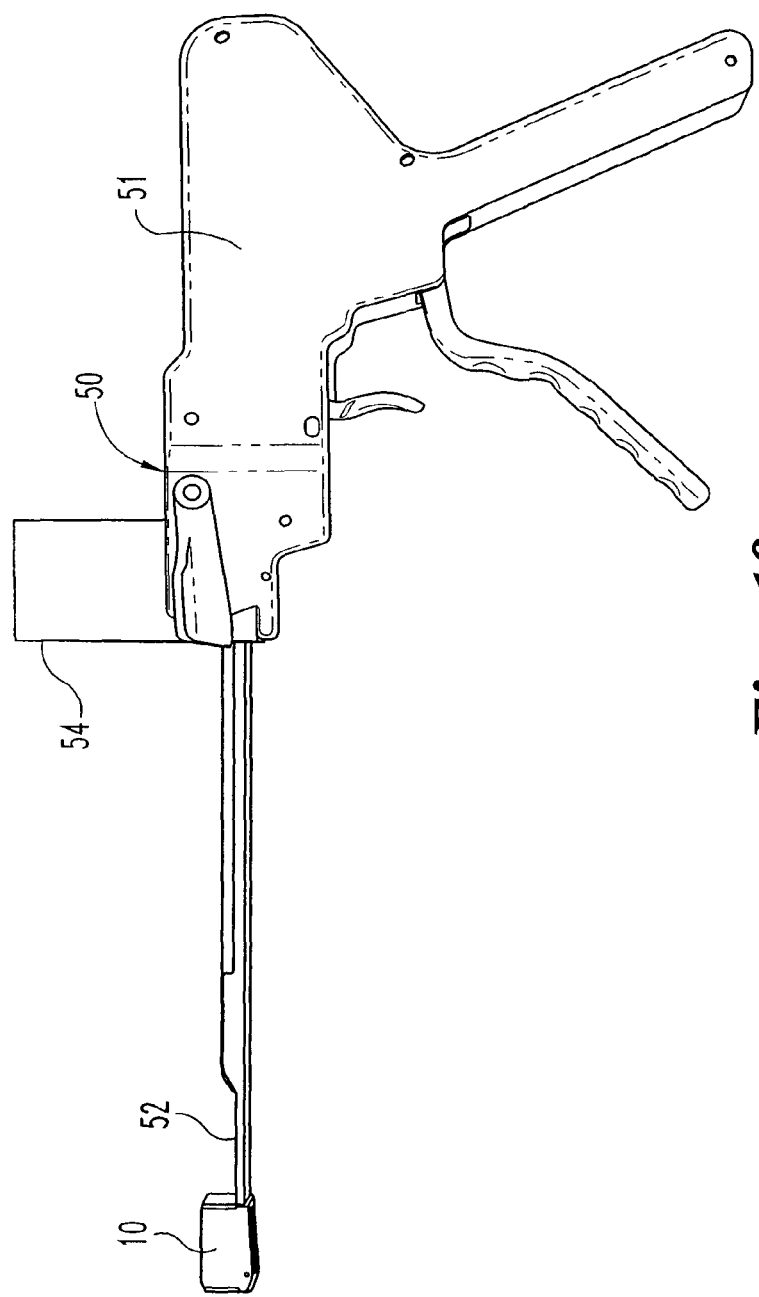
FIG. 10 is a side view of the IBFD and insertion apparatus shown in FIGS. 3-4.

As shown in FIGS. 9, 10 and 12, the wafer inserter apparatus 50 provides an avenue for passage of wafers 55 from a wafer cartridge 54 into the IBFD. The inserter apparatus includes a cartridge gun that extracts wafers 55 consecutively from a stack within the cartridge 54 and conveys them along the track 52 to the IBFD. As shown in FIGS. 11a-b, the wafers 55 are configured for transport along the track 52 and for interlocking engagement within the IBFD. In particular, the wafers include a leading bevel 56 and an opposite trailing bevel 57 to facilitate movement of each successive wafer underneath the immediately prior inserted wafer. The bevels 56, 57 help the incoming wafer dislodge and slide underneath the wafer stack already resident within the IBFD. In certain embodiments, a wafer driver 65 may be provided within the wafer track 52 to advance each wafer into the wafer cavity. The driver 65 can also help hold the lowermost wafer of the stack in position as the inserter apparatus 50 is removed.

The wafers 55 also include interdigitating upper and lower surfaces 58, 59, respectively. The surfaces can assume a variety of configurations intended to prevent relative longitudinal movement between wafers in the stack as well as for lateral and rotational stability. The wafers 55 and their respective surfaces can be constructed as disclosed in U.S. Pat. No. 6,595,998 cited above. The disclosure of this patent, and most particularly its discussion of the construction of the wafers, is incorporated herein by reference. In the preferred embodiment, the upper surface 58 defines a ridge 60 and spaced rib 61 extending along the longitudinal axis of the wafer. Similarly, the lower surface defines a linear trough 62 that receives the ridge 60, and a notch 63 that receives the rib 61.

The insertion configuration for the IBFD and wafer inserter apparatus is generally depicted in FIG. 12. The wafer track 52 of the inserter apparatus engages the IBFD with the track end 53 contacting the proximal faces of both the inferior endplate 14 and the superior endplate 12. A wafer 55 is shown resting on the wafer support surface 49 of the track connector 46'. The track connector 46 rests on the support rail 40 (see FIG. 6) with its posts 47 projecting downward toward the post openings 44 in the inferior endplate 14. As shown in the figures, the posts do not necessary extend into the openings 44. Instead, the post openings 44 facilitate the assembly of insertion apparatus to the track connector prior to use.

Figure 14A:
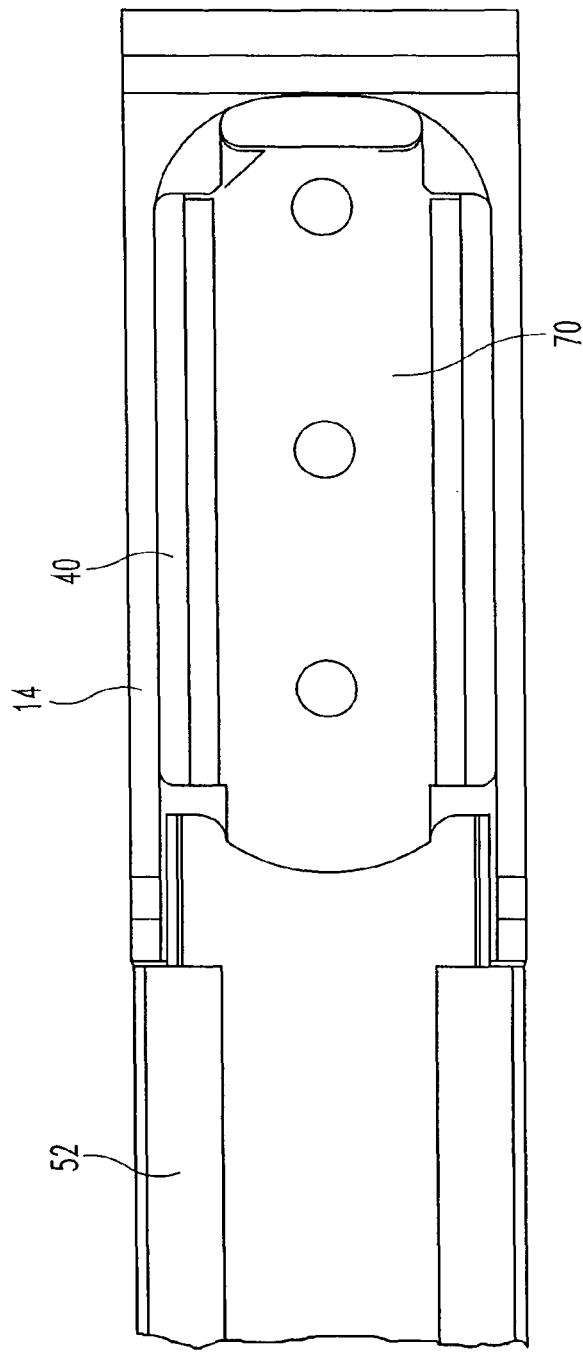
FIGS. 14a-c are top, top perspective and top-perspective cut-away views of components of the insertion apparatus engaged with the inferior endplate portion of the IBFD illustrated in FIGS. 6-7 and including the distal end of the wafer track shown in FIG. 13.
Figure 14B:
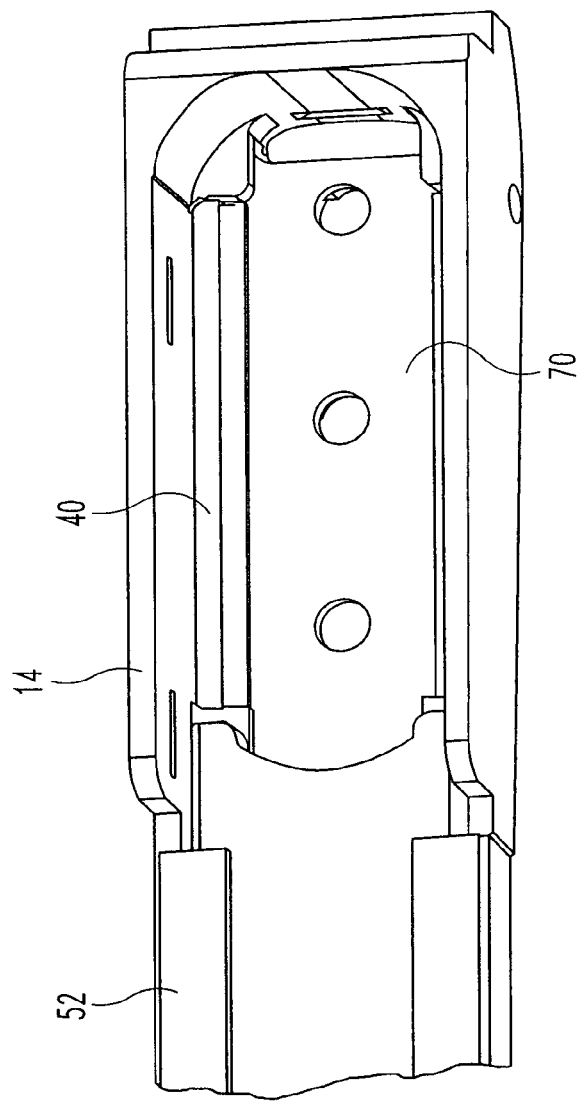
Figure 14C:
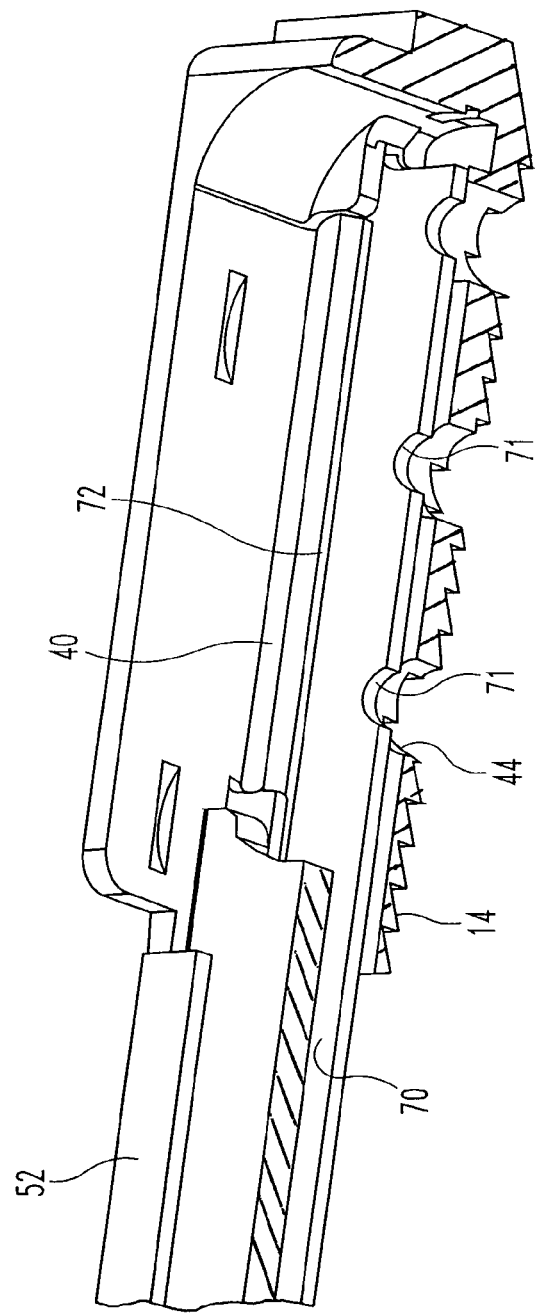

Beneath the track connector 46 reside an insertion plate 70 and a release plate 75 immediately adjacent the connector 46. Both plates provide openings to receive the connector posts 47 therethrough, including openings 71 in the insertion plate and openings 76a-c in the release plate. The insertion plate 70 may define a release track 72 (as shown in FIG. 14c) within which the release plate 75 slides. The release track may be provided to increase the stiffness of the insertion plate, or may be eliminated to permit a reduction in width of the components.

Figure 13:
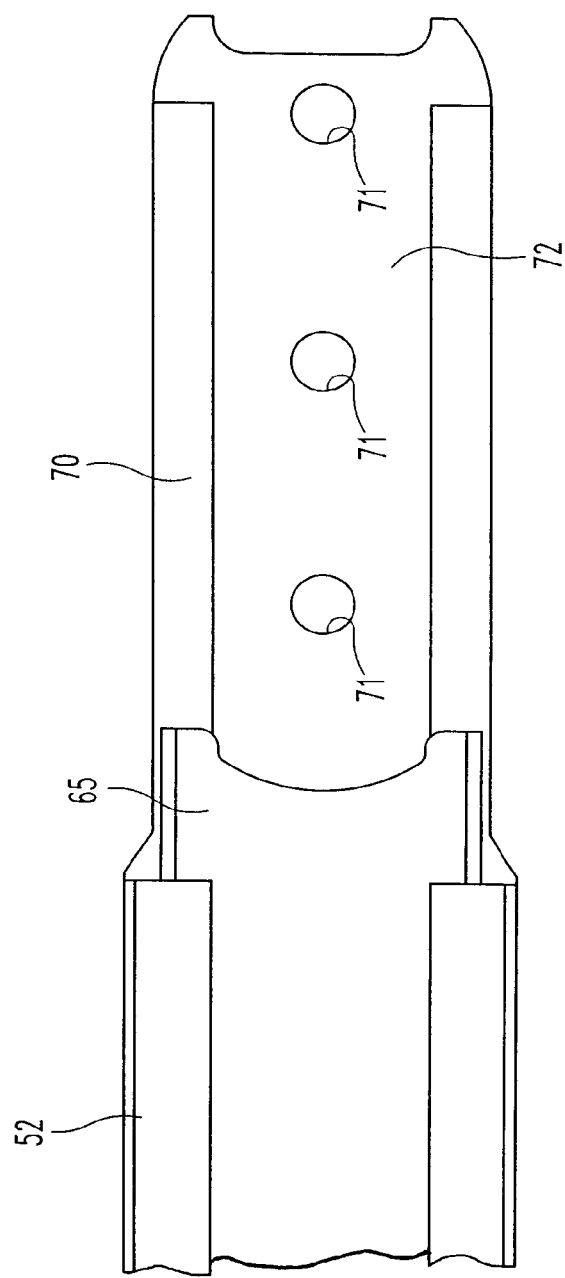
FIG. 13 is a top view of the distal end of the wafer-track portion of the insertion apparatus shown in the prior figures.

The assembly of the components of the inserter apparatus 50 within the IBFD 10 is depicted sequentially in FIGS. 13-18. The insertion plate 70 is shown in FIG. 13. Preferably, the plate 70 is integral with the wafer track 52. As shown in FIG. 12, the insertion plate 70 essentially supports the IBFD with the plate 70 extending into the wafer cavity and the track end 53 abutting the IBFD. This plate 70 will be removed with the inserter apparatus 50, leaving the IBFD within the interbody space. The post openings 71 are sized to receive the connector posts 47 therethrough. As can be seen in FIGS. 14a-c, the insertion plate 70 sits below the support rail 40 in the inferior endplate 14 with its post openings 71 aligned with the post openings 44 in the endplate 14.

Figure 15A:
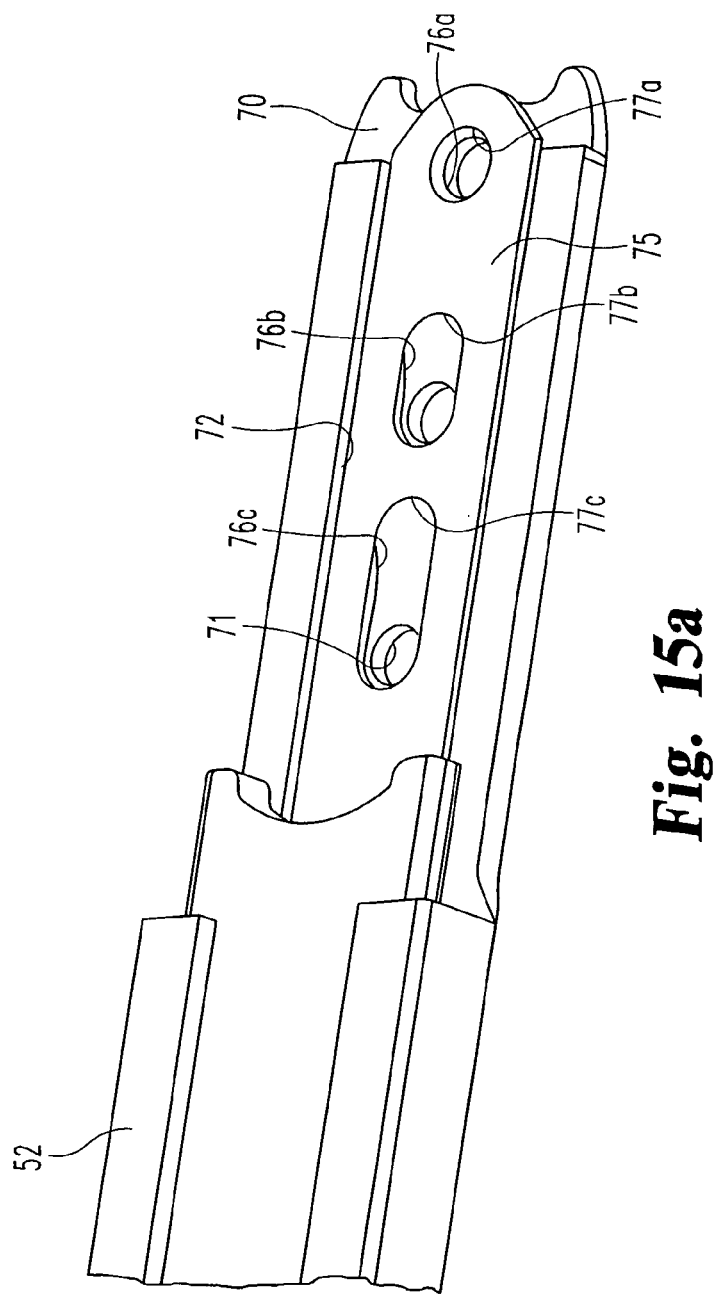
FIG. 15a is a top perspective view of a release plate, driver and the distal end of the wafer track of FIG. 13.
Figure 15B:
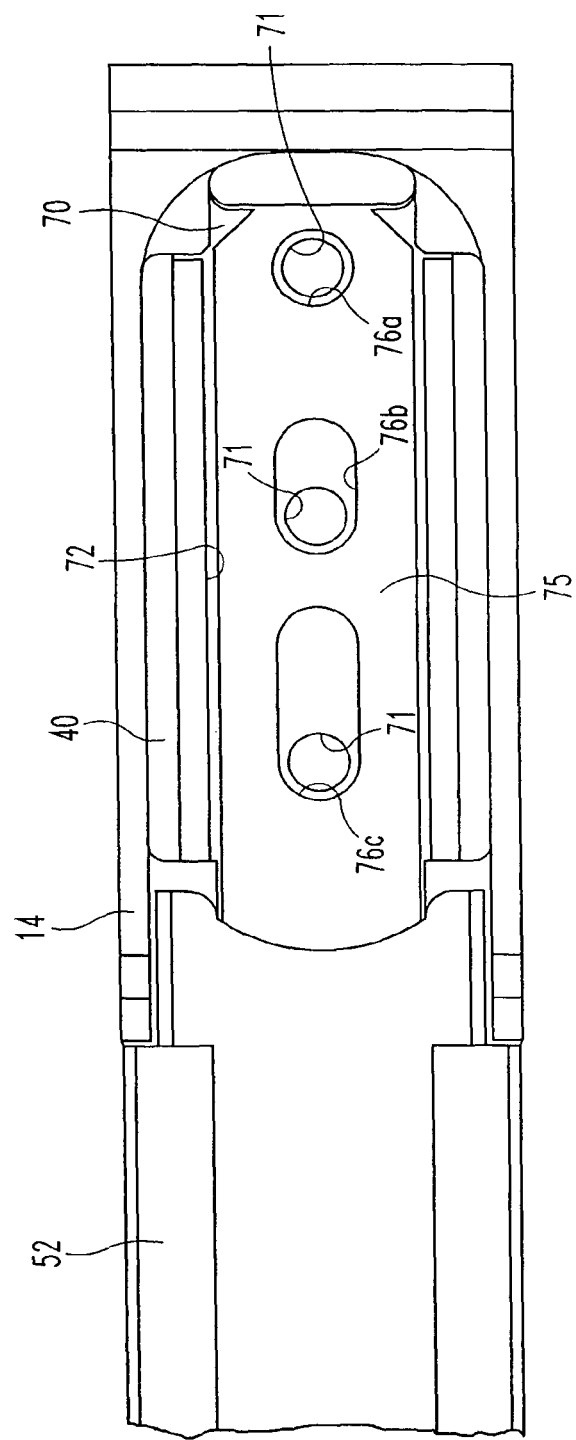
FIG. 15b is a top view of components of the insertion apparatus engaged with the inferior endplate, including the release plate of FIG. 15a. The track connector is removed to show the position of the release plate and the distal end of the wafer track in the inserter cavity.

The release plate 75, as shown in FIGS. 15a-b, is slidably disposed within the release track 72 in the insertion plate 70.

In an alternate embodiment, the release plate 75 is slidably disposed on top of the insertion plate 70 without any release track 72. The release plate 75 includes openings 76*a-c* corresponding to each of the connector posts 47. The distal edge 77*a-c* of each opening is sharpened so that they will sever the posts 47 from the connector plate 46 when the release plate is pulled proximally, or out of the IBFD. The opening 76*a* is generally sized slightly larger than the post 47, while the other two openings 76*b-c* are increasingly elongated. This configuration allows the distal-most post to be cleanly severed before the middle post is severed, and the middle post to be severed before the proximal post. This approach reduces the force needed to sever the posts. Once the posts are severed, they are retained within the post openings 71 via an interference fit, since they are no longer needed to hold the track connector within the IBFD. When the posts are severed, the inserter apparatus 50 can be removed from the implanted IBFD without risk of retracting the IBFD.

Figure 16D:
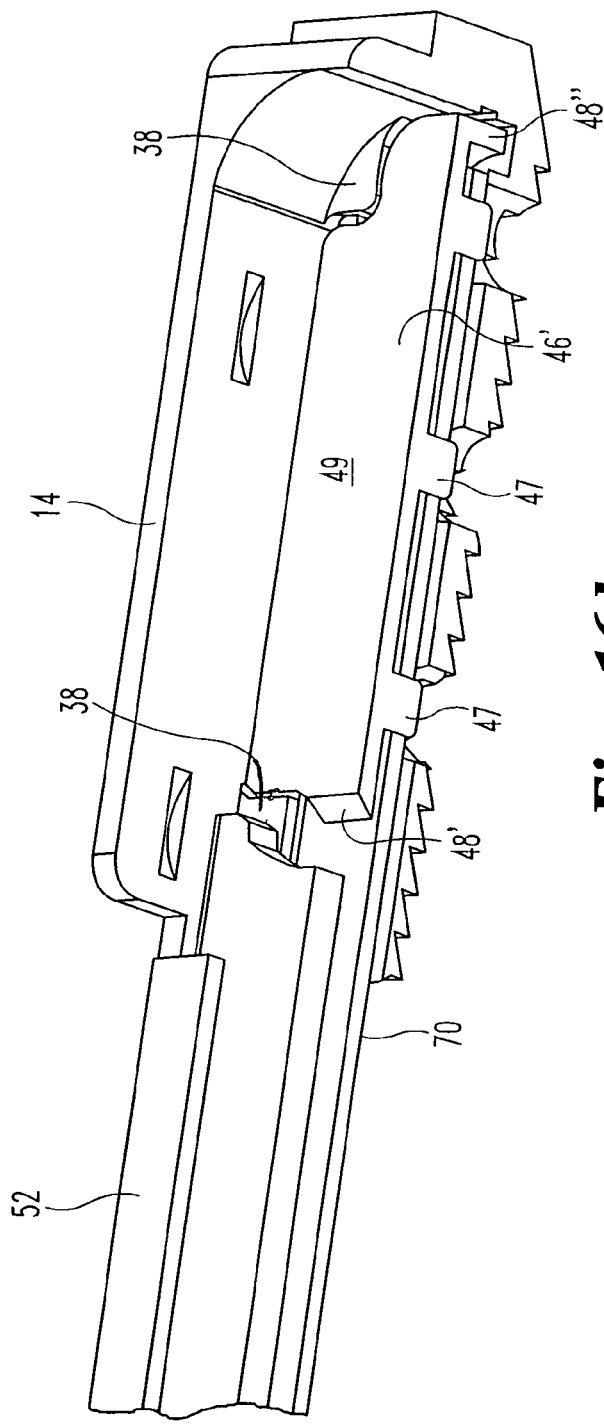
Figure 17:
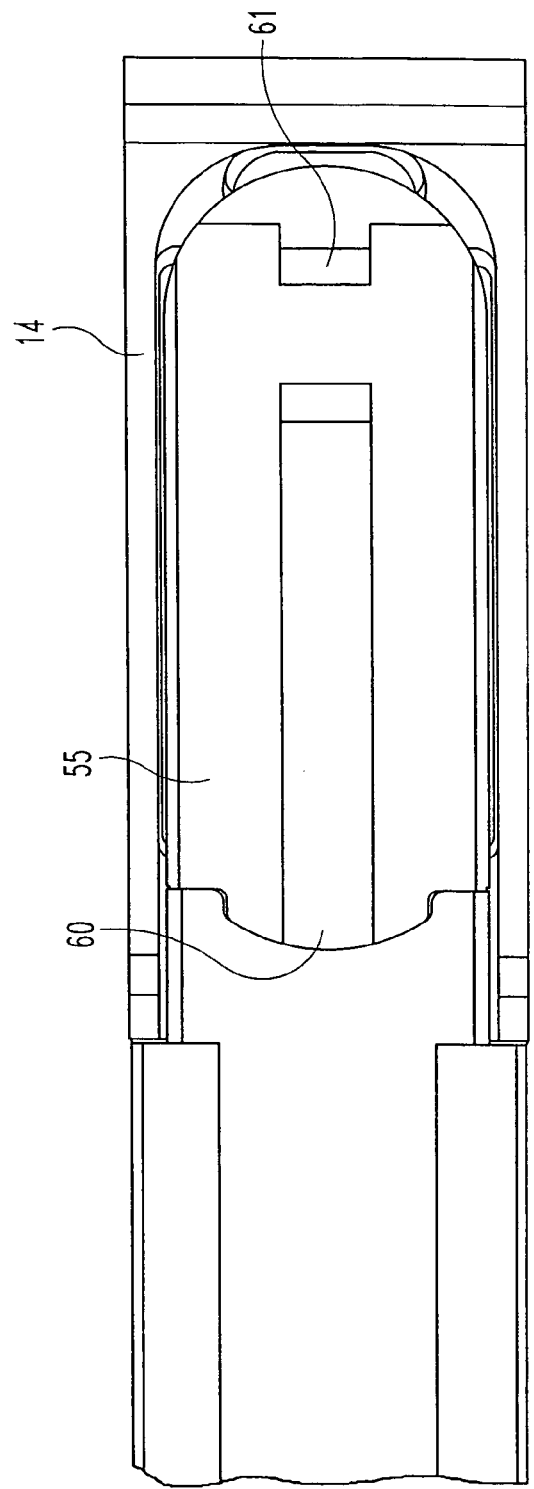
FIG. 17 is a top view of the insertion apparatus with a wafer situated within the inferior endplate portion of the IBFD. The superior endplate is removed to show the position of the wafer in the wafer cavity.
Figure 18:
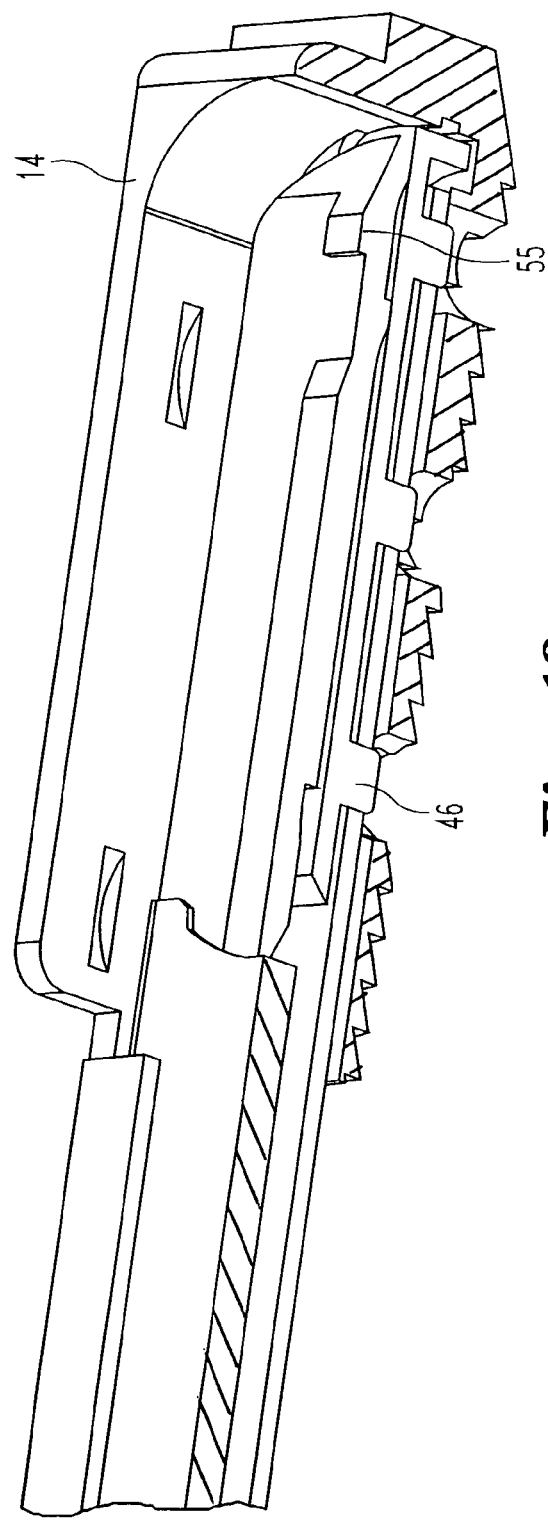
FIG. 18 is a perspective cut-away view of the insertion apparatus, the inferior endplate portion of the IBFD, including the track connector, and wafer shown in FIG. 17.
Figure 19:
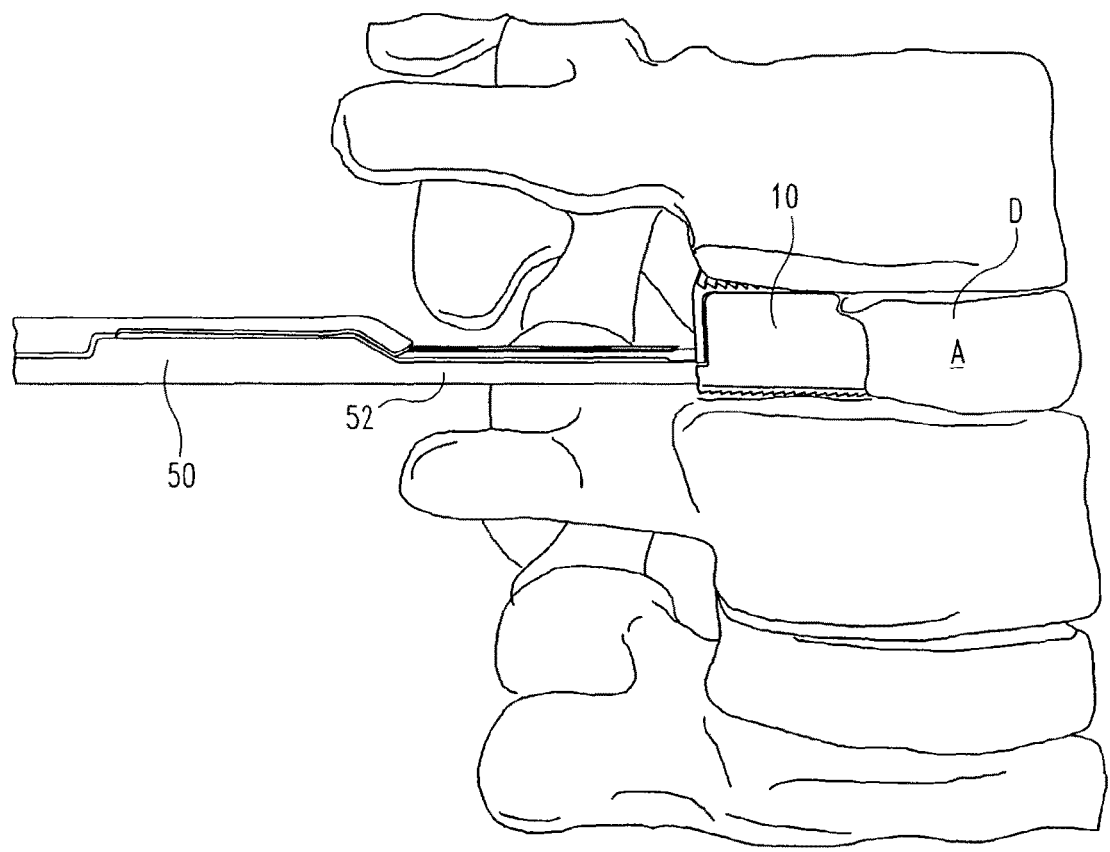
FIG. 19 is a side pictorial view of the insertion apparatus being used to insert an IBFD in accordance with the present invention into an intervertebral space.

The next series of figures, FIGS. 16*a-d*, show the placement of the track connector on top of the insertion plate 70 and release plate 75. As can be seen in FIG. 16*d*, the wafer support surface 49 is generally contiguous with wall 38 of the inferior endplate 14. In an alternate embodiment the wafer support surface 49 is superior to wall 38 of the inferior endplate 14. This alternate embodiment ensures that the compressive load from the wafer stack is transmitted through the wafer support surface 49 and not through wall 38. A first wafer 55 is added in FIGS. 17-18.

The inserter apparatus 50 and the IBFD 10 are shown in position for implanting the IBFD within an interbody space. It is contemplated that the interbody or intradiscal space will be prepared in a known manner. In particular, the disc nucleus is removed by known means, preferably leaving the disc annulus A relatively intact. A portal is formed in the annulus that is sized to the dimensions of the IBFD 10 in its un-expanded configuration (as shown in FIGS. 1-2).

Figures 20A, 20B, 20C:
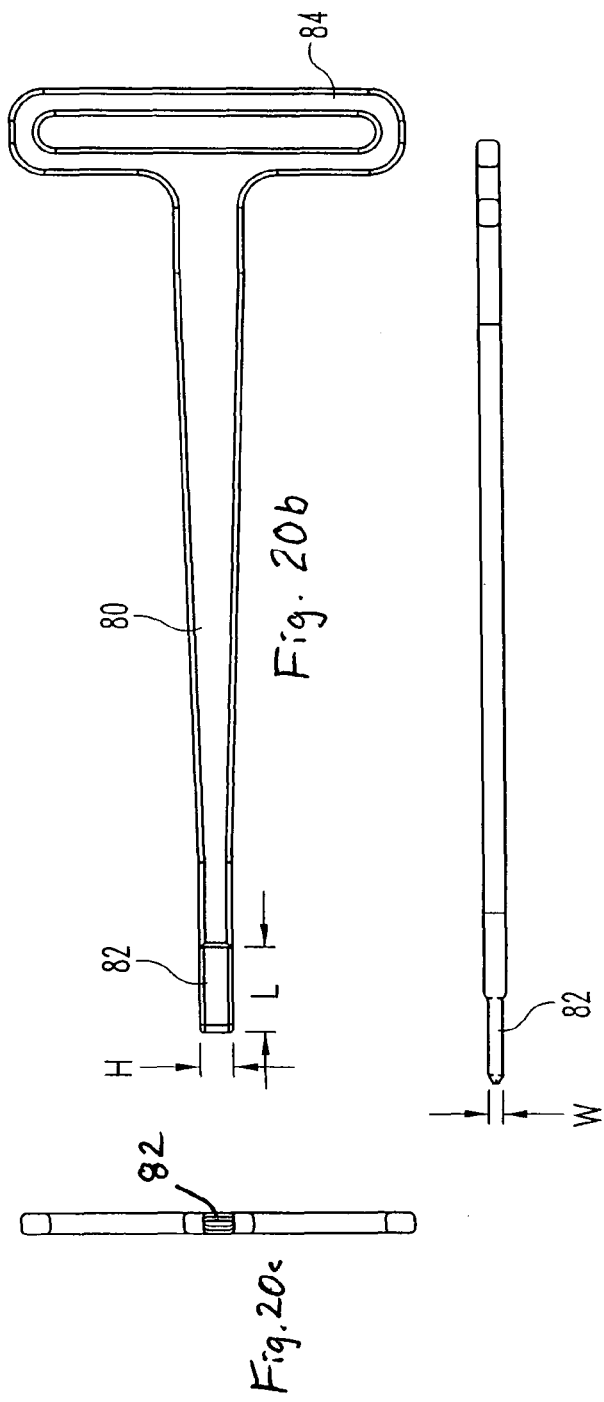
FIGS. 20a-20c include side, top and end views of a disc space distractor for use with the insertion apparatus shown in the above identified figures.
Figure 21C:
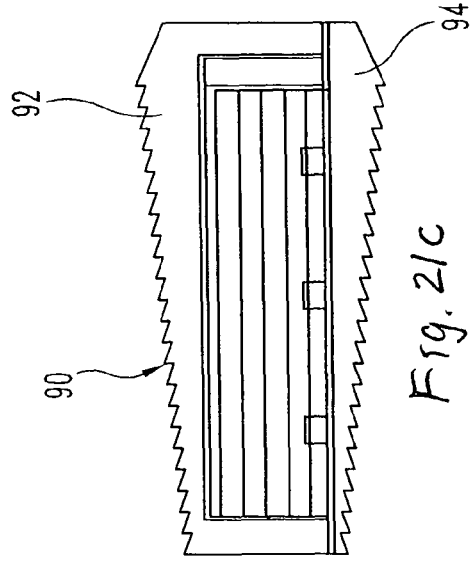
FIGS. 21c-21d are side and end cross-sectional views of the IBFD shown in FIGS. 21a-21b stacked to a different height in which all of the wafers are contained within the endplates.
Figure 21A:
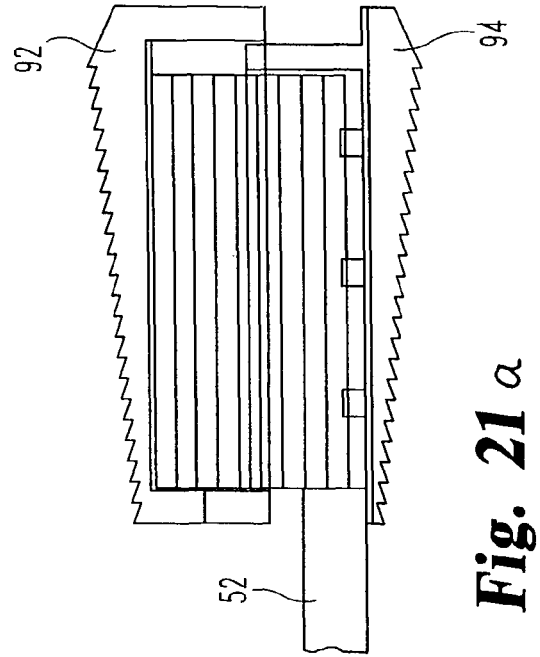
FIGS. 21a-21b are side and end cross-sectional views of an IBFD in accordance with one embodiment of the present invention with a stack of wafers introduced therein to one pre-determined height.
Figure 21D:
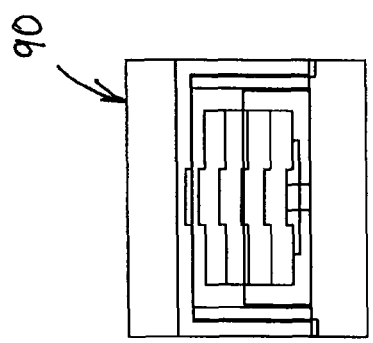
Figure 21B:
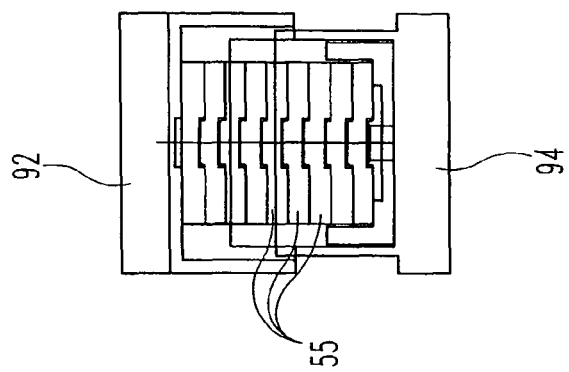
Figure 23A:
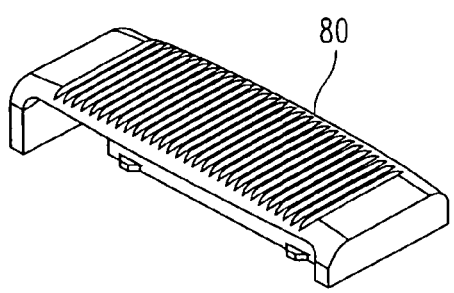
FIGS. 23a-23d include top and bottom perspective views, a side view and a cross-sectional view of a superior endplate for a sagittally curved embodiment of an IBFD of the present invention.
Figure 23B:
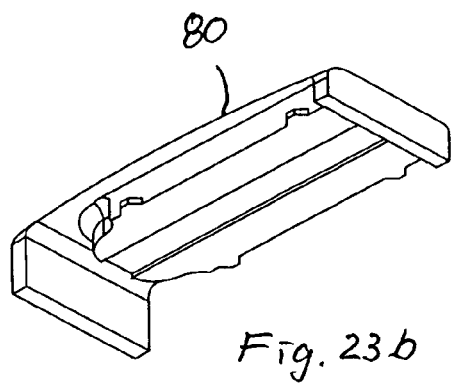
Figure 23C:
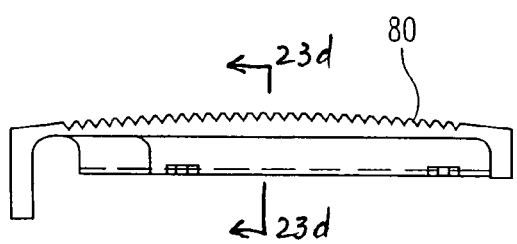
Figure 23D:
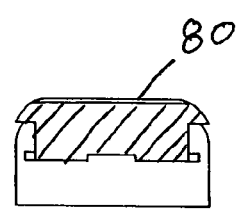
Figure 24D:
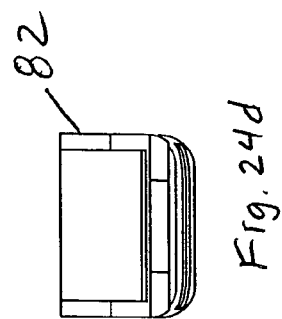
FIGS. 24a-24d include side, top perspective, top and end views of an inferior endplate for a sagittally curved embodiment of an IBFD of the present invention.
Figure 24C:
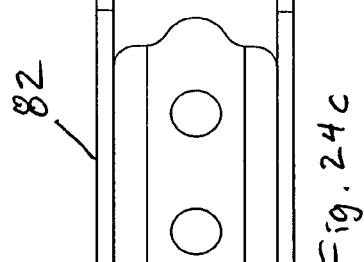
Figure 24A:
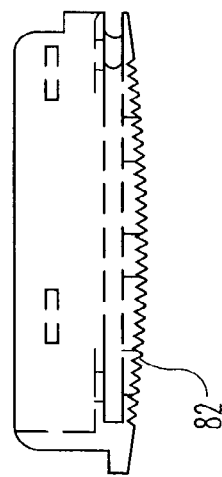
Figure 24B:
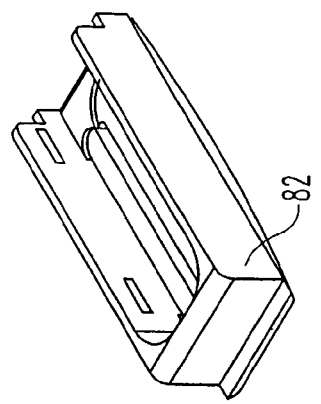

In the preferred arrangement, the IBFD is sized to be received in the unexpanded state through the portal into the disc space without any pre-distraction. In certain situations where the disc space height is smaller than the height of the unexpanded IBFD, pre-distraction may be used to slightly elevate the disc space so as to allow receipt of the unexpanded IBFD through the portal. Such pre-distraction, which can occur using conventional techniques, is not intended to achieve the final disc space height. One approach is to use the distractor 80 shown in FIGS. 20*a*-20*c*. This distractor includes a distal end 82 having a height H greater than its width W. The height H of the distal end 82 is substantially constant over the insertion length L. The distractor is inserted into the disc space at a location adjacent to but laterally spaced from the location where the IBFD is to be inserted with its larger dimension parallel to the vertebral endplates. As such, no distraction occurs during insertion of the distractor 80. The handle 84 is used to rotate the distractor 80 until the larger dimension contacts and pushes apart the vertebral endplates. The distractor 80 can be held in position as the IBFD is maneuvered into the interbody space using the inserter apparatus 50. After removal of the distractor, a second IBFD may be inserted adjacent to the first implanted IBFD.

As shown in FIGS. 21*a-d* and FIGS. 22*a-d*, the IBFD can be expanded to a specific height, with its height being determined by the number of wafers 55 inserted into the IBFD. In the preferred embodiment, the superior and inferior endplates 12, 14 and the wafers have a pre-determined height or thickness. As explained above, the endplates include overlapping portions to help stabilize the stack, in particular the end walls 24 and 32. After implanting the IBFD a biomaterial, such as bone chips or other osteogenetic materials, such as bone morphogenic proteins or adipose-derived adult stromal cells, may be introduced adjacent to or in contact with the IBFD so as to promote fusion between the opposing vertebrae.

As indicated in the figures, in certain embodiments of the invention, the stack height will change when the inserter apparatus is dislodged from the IBFD and removed. In particular, the wafer stack will shift slightly downward when the insertion plate and release plates are removed, allowing the track connector 46 to drop down.

The IBFD 90 shown in FIGS. 21*a-d* and FIGS. 22*a-d* includes superior and inferior endplates 92, 94 that are angled. These endplates are configured to restore or maintain a particular angle of the vertebral motion segment. For instance, if the IBFD 90 is used in the lumbar spine, the endplates are defined at a lordotic angle. The endplates 80, 82 in FIGS. 23*a-d* and FIGS. 24*a-d* are also configured to have arcuate upper and lower surfaces for introduction into and anatomical support of the lumbar spine.

Figure 25A:
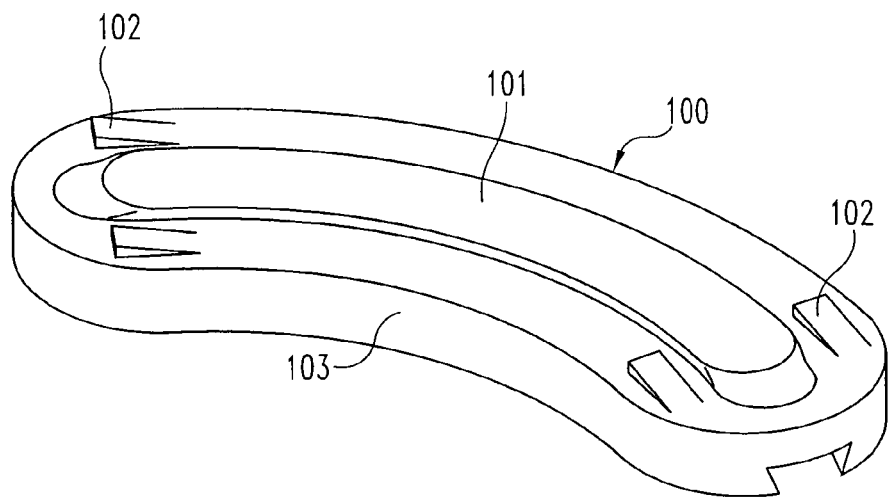
FIGS. 25a-c are perspective, top and cross-sectional views of a transversely curved wafer for use with an IBFD of the present invention.
Figure 25B:
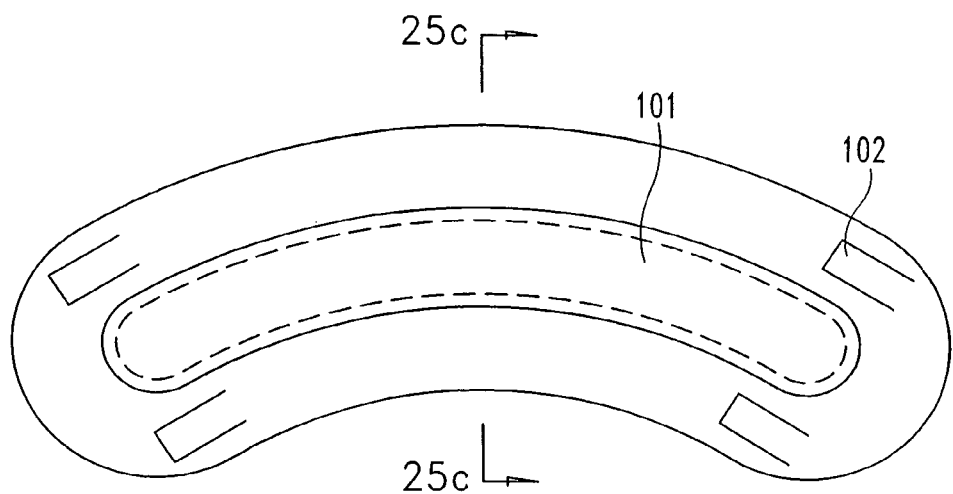
Figure 25C:
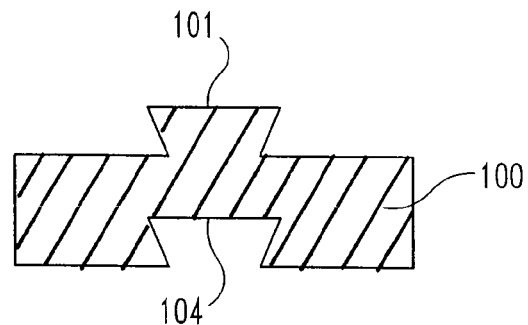
Figure 26:
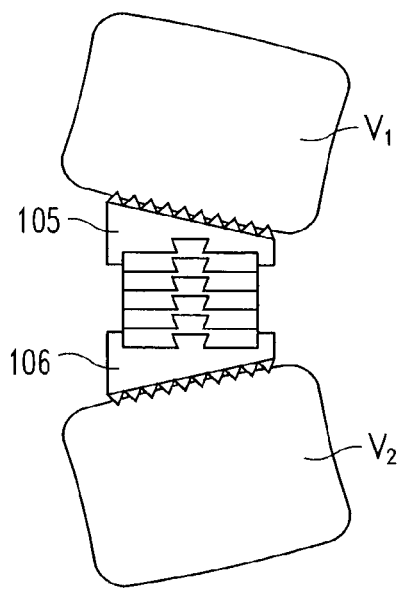
FIG. 26 is a side representation of an IBFD implanted in an intervertebral space with wafers as shown in FIGS. 25a-c.

Alternative concepts for the endplates and the wafers are shown in FIGS. 25*a*-27*d*. In FIGS. 25*a-c*, a curved wafer 100 is provided. The wafer includes interlocking dovetail features 101 and 104 and locking notches 102 to help hold the wafer stack together. As shown in FIG. 26, the endplates 105, 106 can be angled to restore the lordotic angle of the motion segment with the wafer stack therebetween.

Figure 27A:
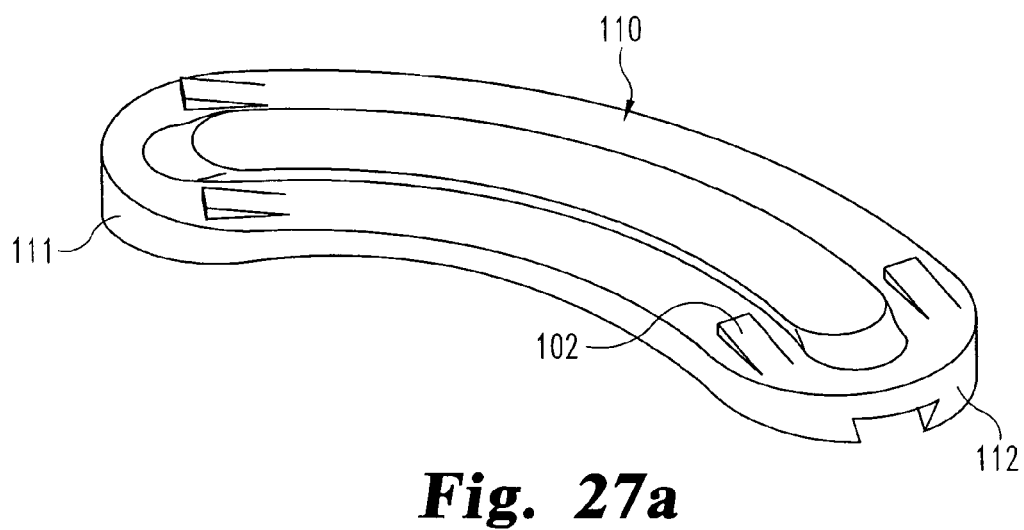
FIGS. 27a-c are perspective, top and cross-sectional views of a transversely curved and angled wafer for use with an IBFD of the present invention.
Figure 27B:
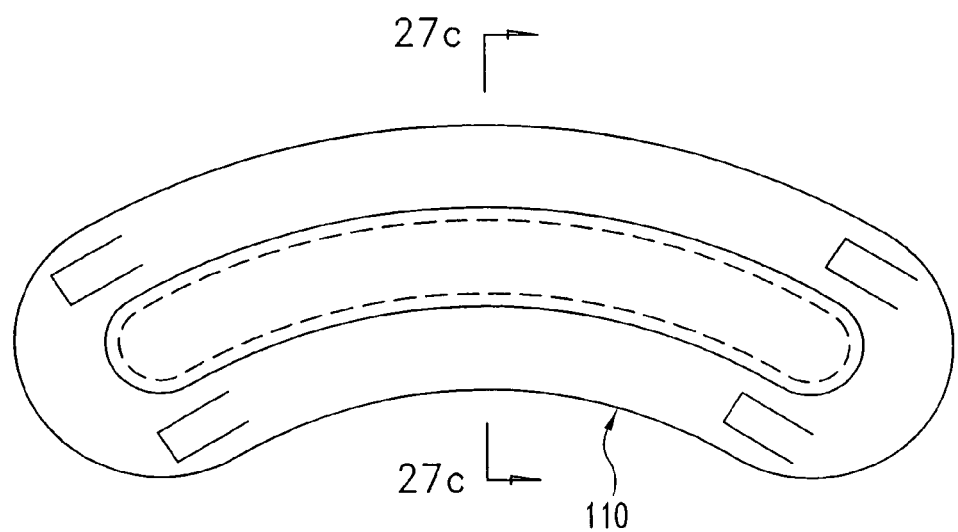
Figure 27C:
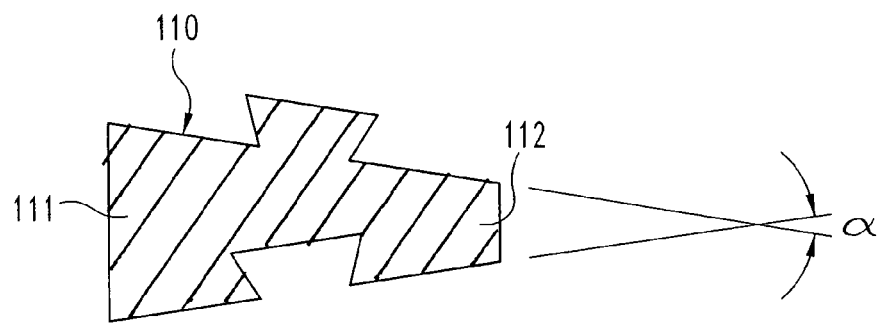
Figure 27D:
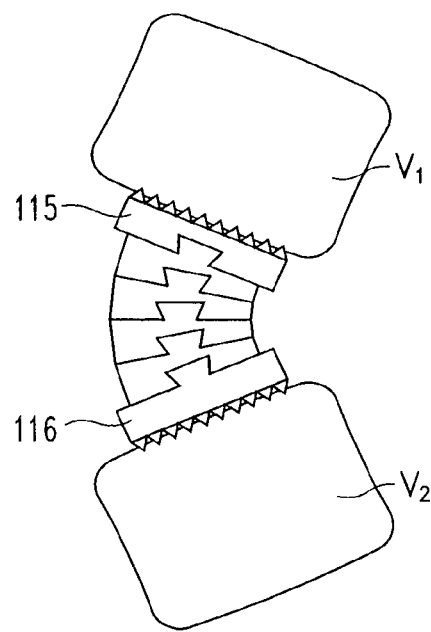
FIG. 27d is a side representation of an IBFD implanted in an intervertebral space with wafers as shown in FIGS. 27a-c.

As an alternative, the wafers can provide the lordotic angle, such as the wafer 110 shown in FIGS. 27*a-c*. The wafer 110 includes one end 111 that is thicker than the opposite end 112. The wafers can be contained within endplates 115, 116 that are planar—i.e., that do not incorporate the lordotic angle.

The wafers 55 shown in FIGS. 11*a-b* include interlocking upper and lower surfaces 58, 59. In particular, with this embodiment, the interlocking features include a ridge 60 and rib 61 that are fed longitudinally into a corresponding complementary shaped trough 62 and notch 63. With this configuration, the stacked wafers resist dislodgement in the fore-aft (longitudinal) degree of freedom and resist relative rotation between adjacent wafers about a vertical axis extending through the stack. The wafers 110 shown in FIGS. 27*a-c* utilize a dovetail interface to interlock adjacent wafers against vertical separation. Neither of these prior embodiments provides a positive interlocking arrangement between adjacent wafers or complete interlocking in multiple degrees of freedom.

An expansion member 160 depicted in FIGS. 28-34 provides a positive interlock between adjacent expansion members that prevents dislodgement or separation in multiple degrees of freedom. As shown in the figures, the expansion member is in the form of an interlocking wafer 160 that is generally planar between the insertion end 162 and the trailing end 164. The insertion end 162 defines an upwardly facing beveled tip 163, while the trailing end defines a downwardly facing beveled tip 165. The beveled tips 163, 165 are configured to contact each other to push one wafer up as the other wafer is introduced into the expandable device, such as the IBFD 10 described above.

The wafer 160 provides interlocking features between the lower surface 170 and the upper surface 190. These interlocking features are configured so that the wafers become positively interlocked as one wafer is introduced beneath the next successive wafer as the wafer stack is formed. Ultimately, every wafer in the stack is positively interlocked with the adjacent wafers above and below. Moreover, the interlocking features are configured so that the interlocking elements mesh smoothly without raising and lowering the adjacent wafer during insertion of a new wafer.

Figure 28:
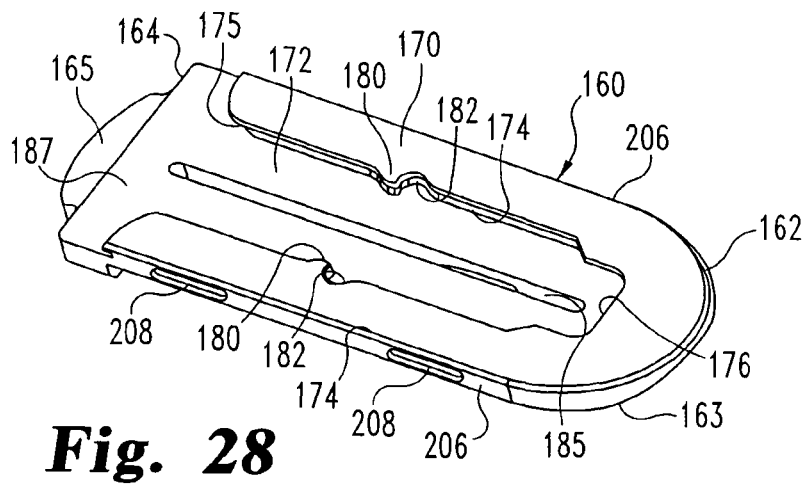
FIG. 28 is a bottom perspective view of an interlocking wafer according to a further embodiment of the invention.

In the preferred embodiment, the lower surface 170 of the wafer 160 defines a recess 172 generally centered along the length or longitudinal axis of the wafer. The recess 172 is open at the trailing end 164 but is preferably closed at the insertion end 162, as shown in FIG. 28. The recess 172 is bounded by opposite side walls 174 and an end wall 176. Part of the interlocking aspect of the wafer 160 is achieved by an entry undercut 175 defined in the side walls 174 at the open entry end of the recess (FIG. 33). The end wall 176 defines a similar undercut 177 (FIG. 34).

Figure 29:
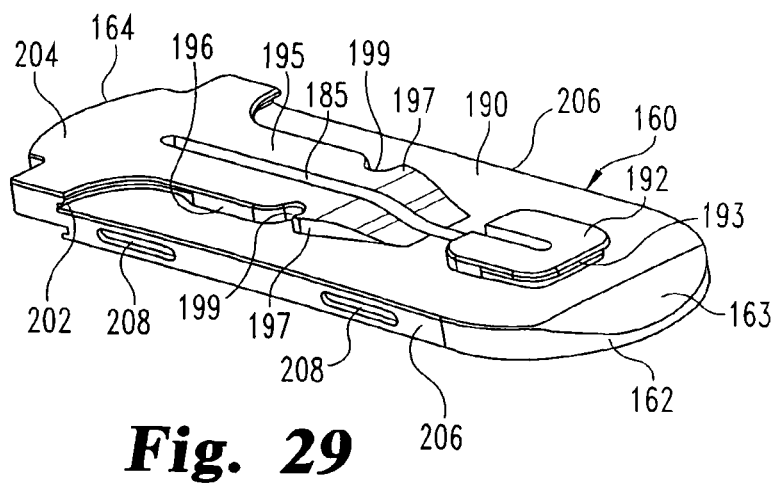
FIG. 29 is a top perspective view of the interlocking wafer shown in FIG. 28.
Figure 30:
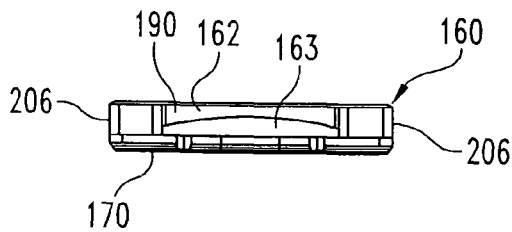
FIG. 30 is an end elevational view of the interlocking wafer shown in FIGS. 28-29.
Figure 35:
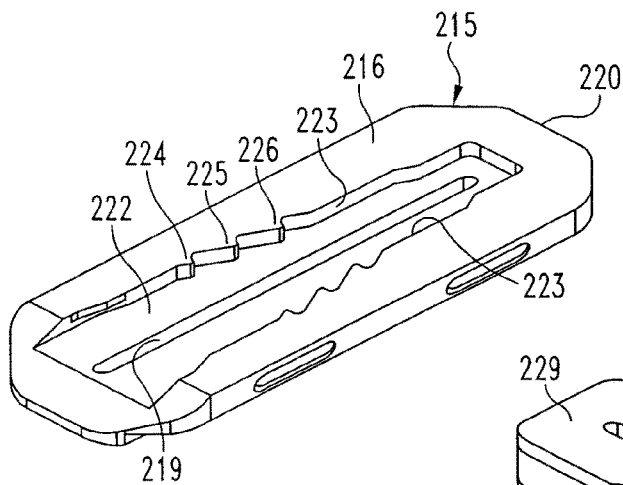
FIG. 35 is a bottom perspective view of an alternative configuration of an interlocking wafer according to the present invention.
Figure 36:
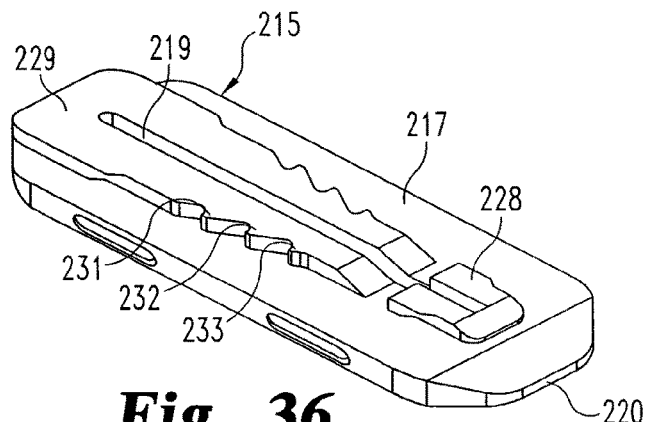
FIG. 36 is a top perspective view of the alternative configuration shown in FIG. 35.

The upper surface 190 of the wafer provides features that interlock with the undercuts 175, 177. In the preferred embodiment, the upper surface 190 includes a leading boss 192 at the insertion end 162 of the wafer, as shown in FIG. 29. The leading boss 192 defines an engaging undercut 193 (FIG. 34) that is sized to fit snugly within the undercut 177 in the end wall 176 of the lower surface 170. The upper surface 190 further includes a trailing boss 195 that extends from the trailing end 164 toward the leading boss 192, but terminating short of the leading boss. The trailing boss 195 includes opposite side walls 196 that are configured for sliding contact with the side walls 174 of the recess 172 in the lower surface of an adjacent wafer to help prevent relative rotational movement of stacked wafers. These opposite side walls form trailing undercuts 202 (FIG. 34) that engage the undercuts 175 in the side walls of the lower surface recess.

Thus, when one wafer slides underneath a previously inserted wafer, the beveled tip 163 at the insertion end 162 contacts the beveled tip 165 of the trailing end 164 of the previously inserted wafer, thereby lifting that wafer to receive the newly inserted wafer. As the new wafer is inserted further, the leading boss 192 travels across the entry surface 187 and enters the recess 172, followed by the trailing boss 195. As the newly inserted wafer continues along the recess, the mating surface 204 aligns with the entry surface 187, and the undercut 193 and undercut 202 substantially simultaneously slide within the corresponding undercuts 177 and 175 in the lower surface 170 of the previous wafer. These engagements between the undercuts in the lower and upper surfaces form part of the interlocking connection between adjacent wafers 160.

A further aspect of the interlocking connection is achieved by resilient latching elements between the lower and upper surfaces 170, 190. In the preferred embodiment, each side wall 174 of the lower surface recess 172 forms a latch element 180 followed by an indentation 182 (i.e., between the latch element and the end wall 176 of the recess). Each side wall 196 of the trailing boss 195 of the upper surface 190 forms complementary latch elements 197 followed by indentations 199 (i.e., between the upper surface latch elements and the trailing end 164 of the wafer). The latch elements 197 are particularly configured for engagement within the side wall indentations 182 in the lower surface recess 172. Likewise, the upper surface indentations 199 are configured to receive the lower surface latch elements 180. This engagement is depicted in FIG. 31, in which wafers 160 and 160' (in phantom) are interlocked with the latch elements 180 engaging the indentations 199' and the latch elements 197' engaging the indentations 182. As can be seen from the figure the latch elements 180 and 197' cooperate to prevent relative fore and aft movement between the wafers 160, 160', as well as relative rotational movement.

The leading boss 192 on the upper surface 190 is sized to pass between the latch elements 180 on the lower surface of the adjacent wafer. However, in order for the interlocking feature to work, the latch elements 197 of the upper surface must have a normal engagement orientation that is wider than the recess 172 between the latch elements 180 of the lower surface 170. Consequently, the present invention contemplates a resilient feature of the wafer 160 that allows resilient deformation of one wafer relative to the other as the latch elements pass by each other. In accordance with this embodiment of the invention, the wafer defines a central slot 185 that passes between the lower and upper surfaces. The slot 185 preferably extends along a substantial portion of the length of the wafer, and most preferably has a length sufficient so that the latch elements 197 are positioned generally at the mid-point of the length of the slot. With this configuration, the slot 185 has its region of maximum deformation where it is needed—at the latch elements. Thus, when one wafer is inserted below a prior wafer, the slot 185 of the newly inserted wafer may constrict as the latch element 197' contacts the latch element 180. Once the latch element 197' reaches the indentation 182, the resilient nature of the wafer allows the slot 185 to spring back to its original width, thereby locking the latch element 197' within the indentation 182.

In a further feature of this embodiment, the wafer 160 includes a pair of pre-load recesses 208 on each side surface 206. The recesses engage complementary projections in the expandable device 250 (FIG. 44) to hold the wafer in a predetermined position until dislodged from below. Details of this pre-load feature follow below in the discussion of the expandable device 250.

A further embodiment of an interlocking wafer 215 is depicted in FIGS. 35-38. This wafer 215 includes a lower surface 216, an upper surface 217 and a thru slot 219 that are similar to the corresponding elements of the wafer 160. The lower surface 216 defines a recess 222 formed by side walls 223. The overall shape of the recess 222 is similar to the shape of the recess 172, except that the single pair of latch elements in the prior embodiment is replaced by three pairs of latch elements 224, 225 and 226.

Figure 37:
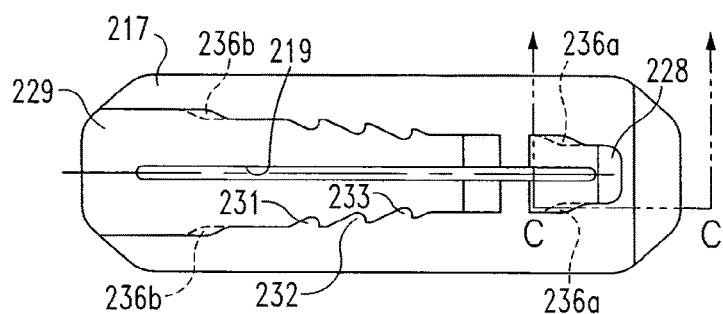
FIG. 37 is a top elevational view of the alternative configuration shown in FIGS. 35-36.
Figure 38:
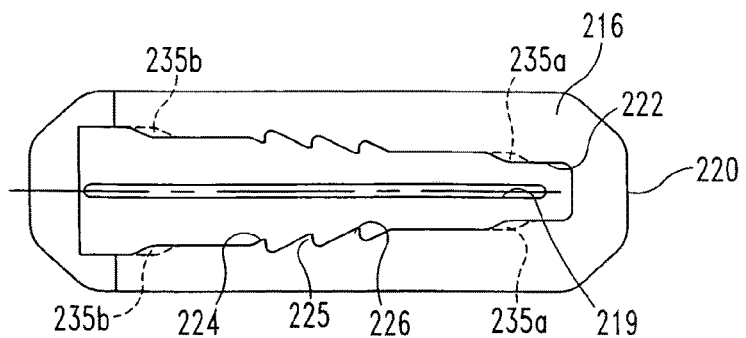
FIG. 38 is a bottom elevational view of the alternative configuration shown in FIGS. 35-36.

The upper surface 217 includes a leading boss 228 and a trailing boss 229 that are also similar to the like elements of the prior embodiment. The trailing boss 229 incorporates latch elements 231, 232 and 233 that are configured to mate or interlock with the latch elements 224-226. As can be seen in FIGS. 37-38, the latch elements 224-226 and 231-233 narrow toward the insertion end 220 of the wafer 215 so that the lateral space between the forward latch elements 226 is narrower than between the middle latch elements 225, which is narrower than the gap between the trailing latch elements 224. This configuration produces a ratcheting effect as a subsequent wafer interlocks with a previous wafer. In addition, the multiple latch elements ensure that adjacent wafers are firmly interlocked to prevent separation when the wafer stack is subjected to in situ forces.

Figure 39:
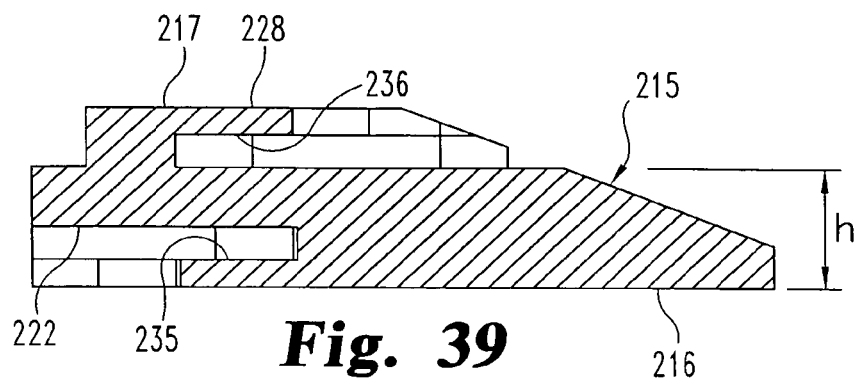
FIG. 39 is an enlarged partial side cross-sectional view of the interlocking wafer depicted in FIG. 37 taken along line C-C as viewed in the direction of the arrows.

While the latch elements interlock the wafers in the longitudinal degrees of freedom, the wafer 215 also includes undercuts to interlock the wafers in the vertical degree of freedom. In particular, in this further embodiment, the recess 222 defines opposite undercuts 235a inboard from the closed end of the recess, as shown in FIGS. 38-39. The leading boss 228 of the upper surface 217 defines complementary undercuts 236a, as shown in FIGS. 37, 39, to mate with the undercut 235a when one wafer is fully inserted into the recess of a prior wafer. Similarly, the trailing end of the recess 222 defines opposite undercuts 235b while the trailing boss 229 defines complementary mating undercuts 236b, which are all similar to the like components on the wafer 160.

Figure 40:
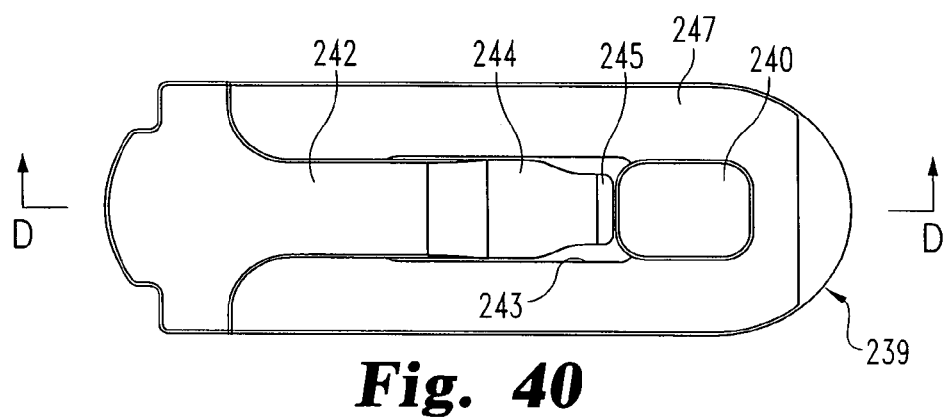
FIG. 40 is a top elevational view of yet another alternative configuration for an interlocking wafer according to the present invention.
Figure 41:
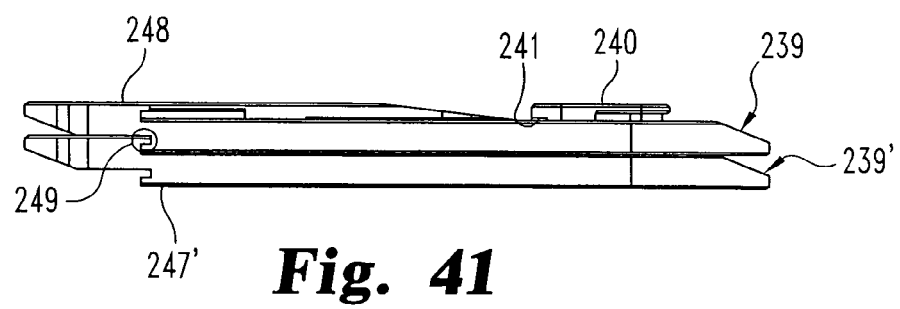
FIG. 41 is a side elevational view of two wafers of the configuration shown in FIG. 40 depicted in their interlocking relationship.
Figure 42:
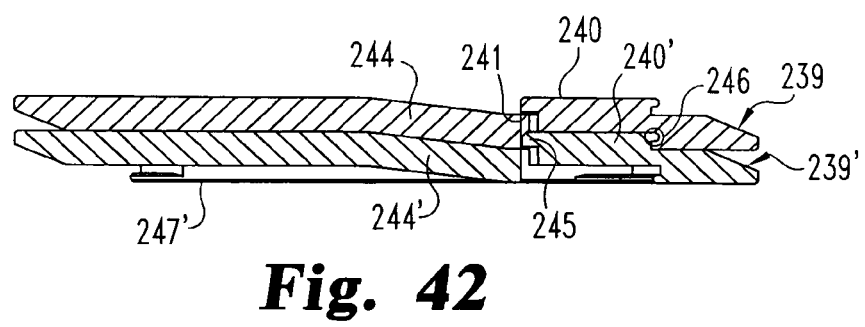
FIG. 42 is a cross-sectional view of the two wafers illustrated in FIG. 41.

Yet another embodiment of an interlocking wafer 239 is illustrated in FIGS. 40-42. The lower surface 247 and upper surface 248 are configured for interlocking engagement, including insertion end mating undercuts 246 (FIG. 42) and trailing mating undercuts 249 (FIG. 41). The wafer 239 includes a leading boss 240 that defines an undercut 241. A wide slot 243 is defined within the wafer from a point below the undercut 241 to a location at the middle of the wafer. A trailing boss 242 is formed in alignment with the slot and includes a flexible portion or arm 244 that is angled into the slot 243. The flexible portion 244 defines an undercut 245 at its tip that is arranged to contact the upper surface 238 at the leading boss 240, as best shown in FIG. 42. When a subsequent wafer 239' is inserted beneath a wafer 239, the leading boss 240' pushes the flexible arm 244 up into contact with the undercut 241 in the leading boss 240 of the upper wafer 239. The flexible arm 244 is then wedged between the leading boss 240 of the upper wafer 239 and the leading boss 240' of the lower wafer 239' to interlock the wafers in multiple degrees of freedom.

The wafer 160 of FIGS. 28-34, the wafer 215 of FIGS. 35-39, and the wafer 239 of FIGS. 40-42 each provide features for interlocking relationship between adjacent wafers. Moreover, these features interlock the wafers in several degrees of freedom, or against relative displacement in several directions. For example, the interlocking latch elements and indentations lock adjacent wafers in shear— i.e., relative movement fore and aft, and side-to-side. The undercuts, 175, 177, 193 and 202, for instance, resist fore-and-aft movement. In addition, the relationship between the latch elements and the undercut interfaces locks the wafers in tension.

One important objective of interlocking in multiple degrees of freedom is to prevent dislodgement of adjacent wafers as a stack is being formed. In certain embodiments, as new wafers are added, the height of the stack increases so that intermediate wafers of the stack are no longer supported by the walls of the IBFD (such as IBFD 10). The unsupported wafers may be susceptible to sliding apart or rotating relative to each other, which may disturb the integrity of the completed IBFD. Interlocking each wafer in the stack forms a substantially rigid stack that extends perpendicularly from the base of the stack upward into contact with the opposing surface. Moreover, interlocking the lowermost wafer to the next adjacent wafer helps hold that lowermost wafer against the insertion force of a newly inserted wafer.

Interlocking the lowermost wafer to the remainder of the stack also helps maintain the lowermost wafer in proper position to receive the next wafer to be added to the stack. It is important that the lowermost wafer not be canted forward or backward. If canted forward, the trailing end 164 of the wafer 160, for instance, will block passage of the next wafer to be introduced. If canted backward, the next wafer will not engage any of the interlocking features so that the prior wafer stack will simply rest unconstrained on the upper surface 190 of the wafer.

As indicated above, each wafer may include pre-load recesses 208 on the side surfaces 206 of the wafers 160. These pre-load recesses are engaged by mating ribs in the inferior component of an expandable distraction device, such as the device 250 shown in FIGS. 43-46. The device 250 includes a superior plate 251 and an inferior plate 252 that are similar in function to the like components of the device 10 described above. The plates 251, 252 may include engagement ribs 254 that are configured to engage the opposing body tissue surfaces to be distracted. For instance, where the device 250 is used for interbody distraction, with or without fusion, the ribs 254 may be configured to engage the vertebral endplates. Other engagement or tissue gripping configurations may also be used, such as, for example, teeth, fins, ridges, threads and various combinations thereof. Additionally, porous surface coatings, indentations or openings may be used to promote bone ingrowth.

Figure 43:
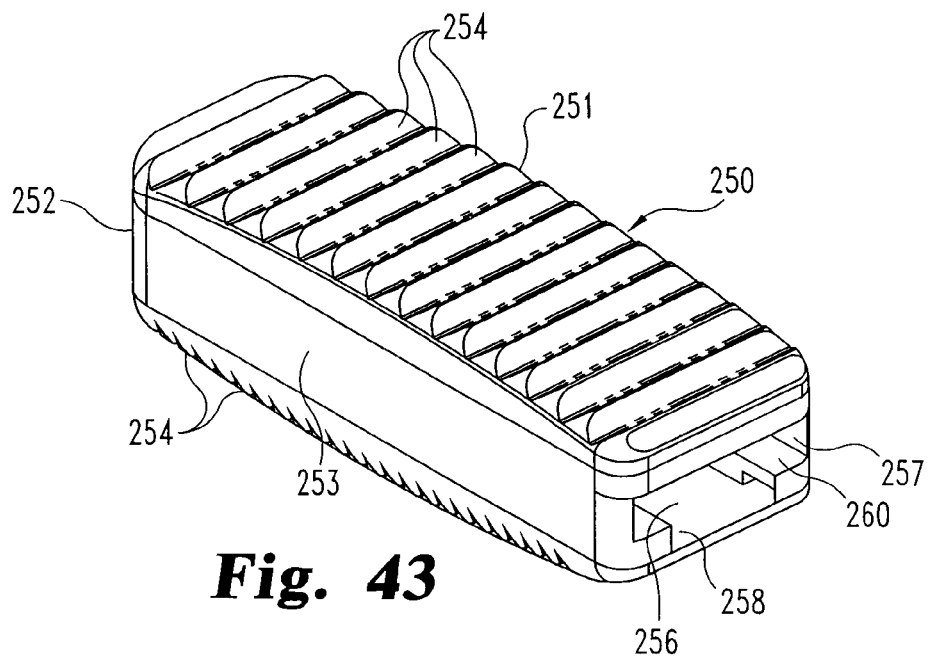
FIG. 43 is a top perspective view of an expandable device configured to receive a series of the wafers shown in prior figures.
Figure 44:
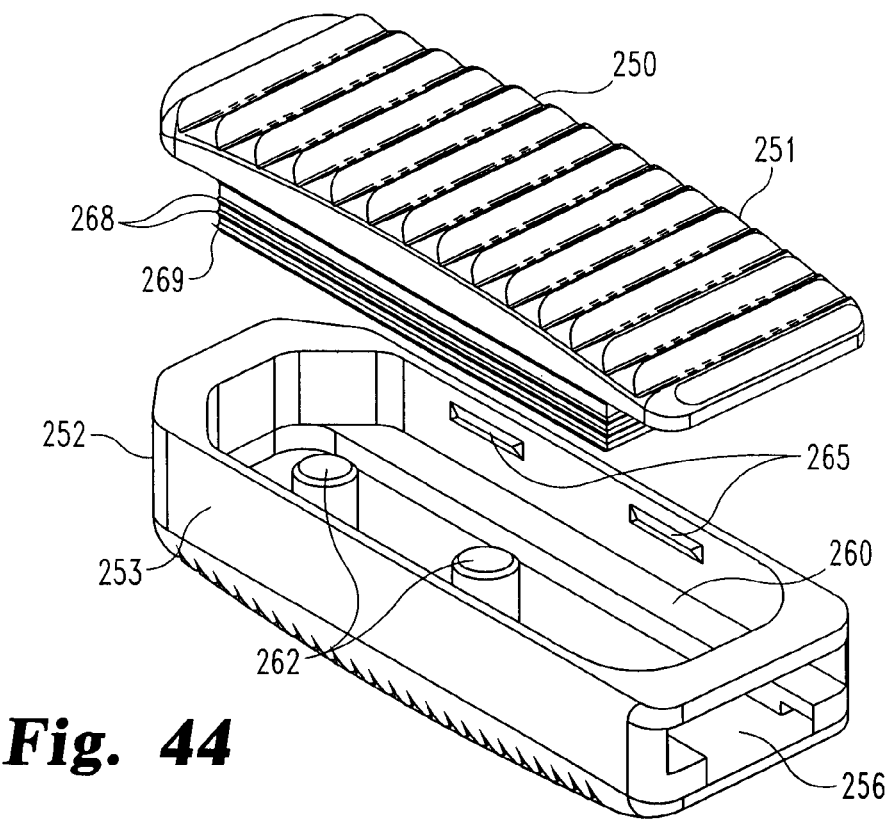
FIG. 44 is an exploded view of the superior and inferior endplate components of the expandable device shown in FIG. 43.
Figure 45:
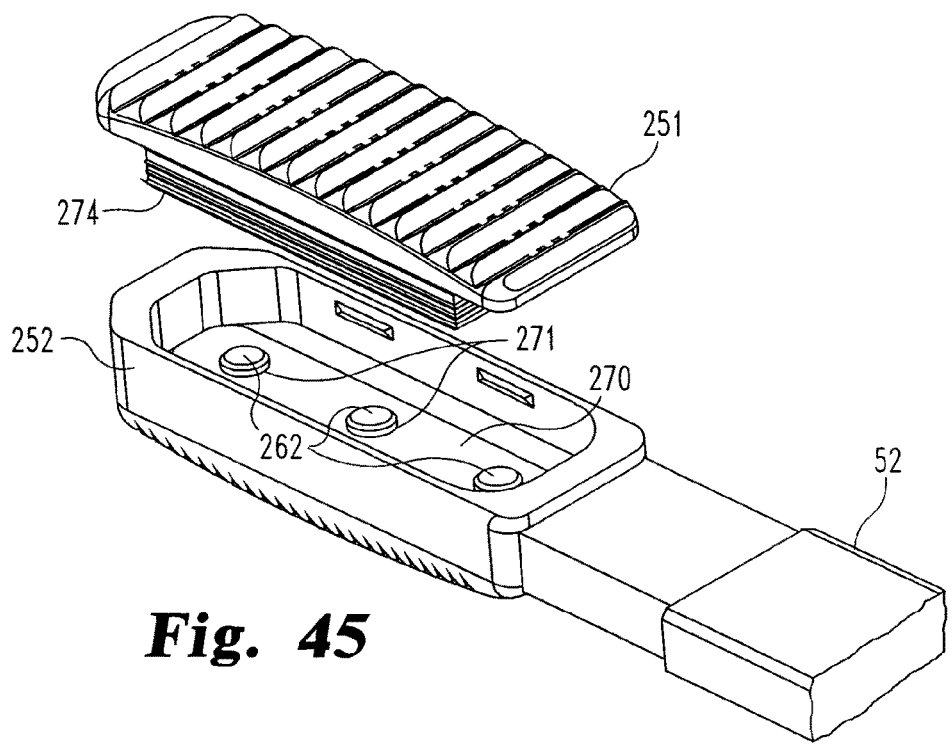
FIG. 45 is a top perspective view of the expandable device shown in FIG. 43 engaged to a wafer inserter apparatus.
Figure 48:
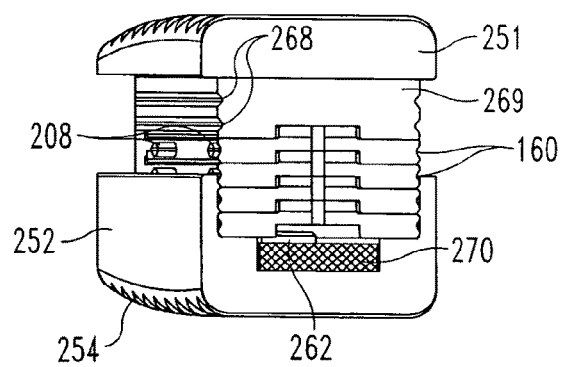
FIG. 48 is an end perspective cross-sectional view of the expandable device and wafers shown in FIG. 46 taken along line E-E.

The superior and inferior plates 251, 252 are similar to the plates of the device 10 in that the plates are initially engaged during insertion into the body space. Thus, in one embodiment, the side walls 253 of the inferior plate 252 define interior projecting ribs 265, while the superior plate 251 defines a series of mating grooves 268 on opposite sides of a lower hub 269 of the plate (FIGS. 44, 48). These ribs and grooves form a releasable engagement feature that initially holds the two plates together, and that is configured to disengage upon pressure from the insertion of the expansion members or wafers. In this embodiment, two rows of grooves 268 are provided, each row configured for a releasable snap-fit with the ribs 265. Thus, when the device 250 is initially provided, as shown in FIG. 43, the superior plate 251 is snapped to the inferior plate 252, with the hub 269 disposed within between the side walls 253 of the inferior plate. It should be understood that only one row of grooves 268 may be formed on the sides of the lower hub 269 such that upon insertion of an initial expansion member or wafer the ribs 265 release from the grooves 268 disengaging the superior and inferior endplates 251, 252.

As shown in FIGS. 43-44, the side walls 253 of the inferior plate 252, together with front end wall 255 and rear end wall 259 form an open, upwardly facing full bounded cavity 261. The inferior plate 252 is open at one end to receive a wafer inserter or track, such as the track 52 (see FIG. 45). Thus, the interior plate defines an insertion channel 256 that includes a wafer channel 257 extending through rear end wall 259 and through which successive wafers may be inserted, and an inserter channel 258. The wafer channel 257 is defined in part by wafer support ledges 260 formed on the inside of each side wall 253, as shown in FIG. 44. The ledges 260 provide a sliding surface for each new wafer being introduced through the track 52 into the device 250, as shown in FIGS. 47-48.

Figure 47:
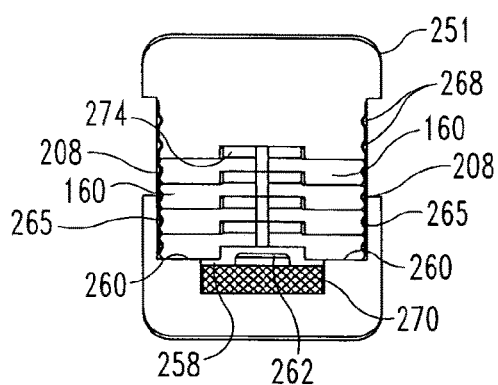
FIG. 47 is an end cross-sectional view of the expandable device and wafers shown in FIG. 46 taken along line E-E.

The function of the pre-load recesses 208 in each wafer 160 is also depicted in FIGS. 47-48. In particular, it can be seen that the lowermost wafer rests on the ledges 260. The next adjacent wafer is restrained by the ribs 265 engaged within the corresponding pre-load recesses 208 on each side of the device. As each new wafer is inserted, it displaces the previous wafer upward until the ribs and recesses interlock. As the ribs and recesses interlock, the displaced wafer assumes a stable and flat orientation so that the interlocking components of the newly introduced wafer will align with the mating interlocking components of the displaced wafer. Another benefit of the ribs 265 and recesses 208 is that this snap-fit type engagement requires a small load to dislodge or disengage. This pre-load may be easily overcome by the introduction of a new wafer underneath the existing stack of wafers. However, the pre-load is sufficiently high that the stack cannot be inadvertently disengaged or moved upward by anatomic forces of extraneous forces occurring during the initial implantation process.

As also shown in FIGS. 47-48, the hub 269 of the superior plate 251 includes wafer mating features 274 that are preferably identical to the features on the lower surface 170 of each wafer 160, for example. When the superior and inferior plates are initially assembled, the hub 269 is disposed within cavity 261 and sits on or closely adjacent to the wafer support ledges 260, with the ribs 265 engaged in the uppermost mating groove 268. When the first wafer is introduced, the interlocking features on the upper surface 190 of the wafer 160 engage the mating features 274 on the underside of the boss 269 while the wafer lifts the boss, and therefore the superior plate 251, upwardly. Once the first wafer is fully introduced into the inferior plate 252, the superior plate has been lifted enough so that the lowermost groove 268, if provided, snaps into engagement with the ribs 265. If there is only one groove 268, the superior plate 251 disengages from the inferior plate 252 upon entry of the first wafer 160. As each successive wafer 160 is introduced, this process repeats itself, with each new wafer becoming fully interlocked with the next preceding wafer. It should be noted that the two lowermost wafers 160, but at least the bottom wafer (as seen in FIGS. 47-48), reside within the cavity 261 of the inferior plate 252, fully contained and constricted by the opposing side walls 253 and the front and rear end walls 255, 259.

This embodiment of the invention contemplates a mechanism for releasably connecting the expandable device 250 to the wafer track assembly 52. This mechanism incorporates a movable element that is operable to disengage the device from the track assembly. Thus, in one arrangement, the inferior plate 252 includes at least one, and most preferably three, upwardly projecting posts 262 (FIG. 44). The track assembly includes an insertion plate 270 that is similar to the plate 70 (FIG. 12) of the previous embodiment. The plate 270 defines a plurality of openings 271, each configured to receive a corresponding post 262 therethrough. Similar to the openings 71 in the plate 70 described above, the openings 271 in the insertion plate 270 may be provided with a cutting edge that is configured to sever the posts 262 when the plate 270 is retracted within the track assembly 52. When the posts are severed, the connection between the inferior plate 252 and the insertion plate 270 is broken, which ultimately releases the inferior plate and device 250 from the track assembly 52. Once the inferior plate is disengaged, the track assembly may be removed while the device 250 is left in situ.

It is understood that the track assembly 52 may be used to help maintain the inferior plate 250 in position between the body tissues to be distracted. Once disengaged, the inferior plate remains within the space, so that the inferior plate essentially acts as a base wafer upon which the wafer stack is built. It is therefore important for the inferior plate 252, acting as a base wafer, to remain stable and steadfast in contact with the inferior tissue surface. When the device 250 is used as an interbody device, the inferior plate 252 must remain in solid, fixed contact with the inferior vertebral endplate, assisted by the engagement ribs 254, or other gripping surfaces or bone ingrowth features, as described above. In one preferred procedure, the opposing endplates are scraped or otherwise reduced to bleeding bone to enhance the temporary and permanent fixation of the device plates 251 and 252 to the adjacent vertebral bodies.

It is contemplated that in certain applications, the tissue space to be distracted will be expanded by expansion of the device 250. Thus, with each new wafer inserted, the force needed to push the wafer underneath the immediately prior wafer may be increased by the force needed to distract the body space. However, if the space to be distracted is less than the un-expanded height of the device 250 (as illustrated in FIG. 43), additional distraction may be required. In that case, a separate distraction instrument may be introduced into the body space and used to temporarily distract the space enough to allow insertion of the device 250. The distractor 80 shown in FIG. 20 may be used to open the space sufficiently for insertion of the device. As the tip is rotated, it forces the opposing tissue surfaces apart.

It is contemplated that the distraction tool 80 would be introduced toward one side of the space to leave adequate room within the heart of the space to receive the expandable device 250. In some embodiments, an additional distraction tool may be used at an opposite side of the space. Once the distraction device has been inserted, the distraction tool 80 may then be removed from the space. In certain procedures, a wider distraction tool tip may be used to temporarily expand the space to the intended distracted height. In this approach, the expandable device 250 would be expanded until the device spanned the pre-distracted space, at which time the distraction tool(s) may be removed.

Figure 46:
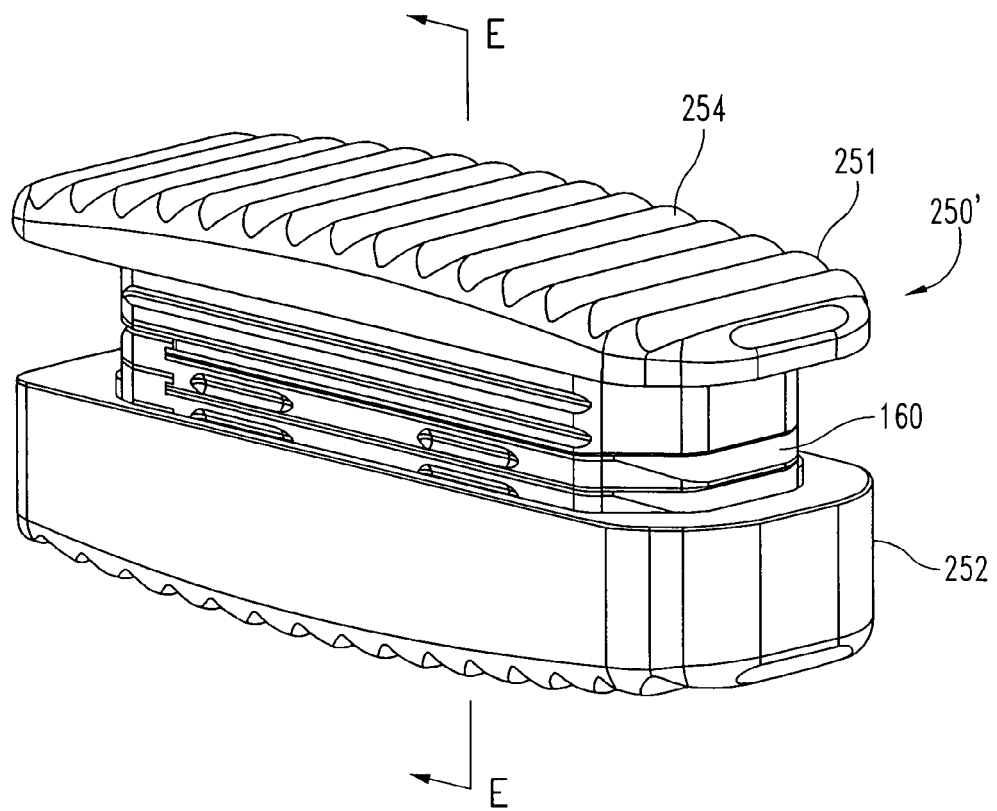
FIG. 46 is side perspective view of the expandable device depicted in FIG. 44, shown in an expanded configuration with a plurality of interlocking wafers disposed therein.

In accordance with certain specific embodiments, the device 250 has a non-expanded height of about 6 mm at its leading (or insertion) end. As shown in FIG. 46, the tissue engaging surfaces of the superior and inferior plates 251, 252 are preferably domed in specific embodiments intended for use in distracting an intervertebral space. The non-expanded domed device then has a maximum height in the center of about 8.5 mm with the engagement ribs. The maximum height of a non-expanded flat device with engagement ribs would be about 7.0 mm over its length. The overall length and width of the device may be calibrated to substantially fill the intervertebral space, or may be preferably sized to leave room around the device for the introduction of filler material around the device. For instance, in one embodiment, the device 250 has a length of about 24 mm and a width of about 9 mm, which leaves sufficient space around the device and within an intact intervertebral disc to pack an osteo-inductive and/or osteo-conductive material. The material may be, for instance, bone chips that are fed into the space around the device 250 using a minimally invasive cannula.

As described above, the interlocking wafers 160, 215 or 239 are configured to add about 1.0 mm to the expanded height of the device 250. For instance, for the wafer 239 shown in FIG. 39, the height h is about 1.0 mm. It is understood that the overall height of the wafer will be greater than the expansion height to accommodate the mating undercuts 235 and 236. The width and length of the wafers is dictated by the interior dimensions of the inferior plate 252 where the wafers are initially introduced into the wafer stack. In a specific embodiment, the wafers have a width of about 7.7 mm and a length of about 20 mm to fit within a correspondingly sized space in the inferior plate 252.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, while the illustrated embodiments have been directed to interbody fusion of the spine, the expandable devices and wafers disclosed herein may be used in other applications that require distraction of tissue surfaces. Modifications in size may be necessary depending upon the body space being distracted.

What is claimed is:

1. An expandable interbody fusion device for implantation into the intradiscal space between the opposing vertebral bodies in a spine, comprising:
   an upper plate including an outer surface and a lower surface generally opposite said outer surface, said lower surface including a beveled surface;
   a lower plate including an outer surface and an inner surface facing said beveled surface on the lower surface of said upper plate, said upper plate being movable in an expansion direction away from said lower plate; and
   an elongate expansion member having a longitudinal axis along its length sized to be received between said upper plate and said lower plate on said inner surface and movable therebetween in a first axial direction along said longitudinal axis that is substantially perpendicular to said expansion direction, said expansion member including thereon first and second axially spaced beveled surfaces and a portion between and interconnecting said first and second beveled surfaces, said portion having an upper surface facing said upper plate and a lower surface facing said lower plate, said expansion member consisting essentially of one fully bounded elongate slot extending along said longitudinal axis through the upper surface and the lower surface of said portion transversely to said expansion direction between and not through said first and second beveled surfaces, said first beveled surface defining a lifting surface extending across said longitudinal axis and operable upon movement of said expansion member in the first axial direction to engage the beveled surface on said lower surface of said upper plate to move said upper plate away from said lower plate in the expansion direction and expand said device.

2. The device of claim 1, wherein said beveled lifting surface on said expansion member faces upwardly toward said upper plate.

3. The device of claim 2, wherein said beveled lifting surface and said second beveled surface are inclined in the same direction along the elongate direction.

4. The device of claim 3, wherein said beveled lifting surface and second beveled surfaces are planar.

5. The device of claim 1, wherein said second beveled surface faces downwardly toward said lower plate.

6. The device of claim 1, wherein said expansion member has a leading end and a trailing end, and wherein said beveled lifting surface is adjacent said leading end and said second beveled surface is adjacent said trailing end.

7. The device of claim 1, further including a locking arrangement to resist movement of said expansion member in incremental positions along said longitudinal axis in a second axial direction opposite said first axial direction upon expansion of said device.

8. The device of claim 1, wherein said upper plate and said lower plate are each elongate, and wherein said upper plate, said lower plate and said expansion member are all oriented in alignment along the first axial direction.

9. An expandable interbody fusion device for implantation into the intradiscal space between the opposing vertebral bodies in a spine, comprising:
   an upper plate including an outer surface and a lower surface generally opposite said outer surface, said lower surface including a beveled surface;
   a lower plate including an outer surface and an inner surface facing said beveled surface on the lower surface of said upper plate, said upper plate being movable in an expansion direction away from said lower plate;
   an elongate expansion member sized to be received between said upper plate and said lower plate on said inner surface and movable therebetween in a first axial direction that is substantially perpendicular to said expansion direction, said expansion member including thereon first and second axially spaced beveled surfaces and a portion between and interconnecting said first and second beveled surfaces, said expansion member consisting essentially of one fully bounded elongate slot extending along a longitudinal axis through an upper surface and lower surface of said portion transversely to said expansion direction between and not through said first and second beveled surfaces, said first beveled surface defining a lifting surface operable upon movement of said expansion member in the first axial direction to engage the beveled surface on said lower surface of said upper plate to move said upper plate away from said lower plate in the expansion direction and expand said device; and
   a locking arrangement to incrementally resist movement of said expansion member during expansion of said device in more than one position along a second direction opposite said first axial direction.

10. The device of claim 9, wherein said locking arrangement comprises a ratcheting structure.

11. The device of claim 9, wherein said upper plate and said lower plate are each elongate, and wherein said upper plate, said lower plate and said expansion member are all oriented in alignment along the first axial direction.

* * * * *